(12) United States Patent
Chiu et al.

(10) Patent No.: US 6,540,734 B1
(45) Date of Patent: Apr. 1, 2003

(54) MULTI-LUMEN EXTRUSION TUBING

(75) Inventors: Jessica Chiu, Palo Alto, CA (US); Paul Reiss, Mountain View, CA (US); Mark Newton, San Jose, CA (US); Eric D. Peterson, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/505,616

(22) Filed: Feb. 16, 2000

(51) Int. Cl.$^7$ .............................................. A61M 25/00
(52) U.S. Cl. .................... 604/508; 604/93.01; 604/523
(58) Field of Search .............................. 604/93.01, 508, 604/523

(56) References Cited

U.S. PATENT DOCUMENTS

| | | |
|---|---|---|
| 3,560,291 A | 2/1971 | Foglia et al. |
| 3,769,117 A | 10/1973 | Bowen et al. |
| 3,974,016 A | 8/1976 | Bondybey et al. |
| 4,069,080 A | 1/1978 | Osborne |
| 4,138,457 A * | 2/1979 | Rudd et al. ............ 264/171.26 |
| 4,156,626 A | 5/1979 | Souder |
| 4,195,637 A | 4/1980 | Gruntzig et al. |
| 4,251,305 A | 2/1981 | Becker et al. |
| 4,323,071 A | 4/1982 | Simpson et al. |
| 4,515,651 A | 5/1985 | Mac Laughlin et al. |
| 4,537,809 A | 8/1985 | Ang et al. |
| 4,581,017 A | 4/1986 | Sahota |
| 4,661,094 A | 4/1987 | Simpson |
| 4,687,430 A * | 8/1987 | Morris et al. ............ 264/209.8 |
| 4,697,575 A | 10/1987 | Horowitz |
| 4,706,652 A | 11/1987 | Horowitz |
| 4,733,047 A | 3/1988 | Cruickshank et al. |
| 4,744,366 A | 5/1988 | Jang |
| 4,748,982 A | 6/1988 | Horzewski et al. |
| 4,762,130 A | 8/1988 | Forgarty et al. |
| 4,763,671 A | 8/1988 | Goffinet |
| 4,771,777 A | 9/1988 | Horzewski et al. |
| 4,771,778 A | 9/1988 | Mar |
| 4,775,371 A | 10/1988 | Mueller, Jr. |
| 4,790,315 A | 12/1988 | Mueller, Jr. et al. |
| 4,793,351 A | 12/1988 | Landman et al. |
| 4,814,029 A * | 3/1989 | Butcher ............ 156/155 |

(List continued on next page.)

FOREIGN PATENT DOCUMENTS

| | | |
|---|---|---|
| DE | 9102312 | 2/1991 |
| DE | 4315002 | 5/1993 |

(List continued on next page.)

OTHER PUBLICATIONS

—Stuart Lindsay et al., "Aortic Arteriosclerosis in The Dog After Localized Aortic X–Irradiation", *Circulation Research*, vol. X, pp 51–60, Jan. 1962.

(List continued on next page.)

*Primary Examiner*—J. Casimer Jacyna
(74) *Attorney, Agent, or Firm*—Blakely, Sokoloff, Taylor & Zafman LLP

(57) ABSTRACT

A multi-lumen balloon for use in a fluted balloon centering catheter and method for providing the same. The multi-lumen balloon maintains a radiation source at the center of a cardiovascular artery, has improved blood perfusion capability, and has improved balloon refolding characteristics. The method of fabricating a multi-lumen balloon designed for a radiation centering catheter uses an improved extrusion process that allows the manufacture of the multi-lumen balloon sub-assembly to be done separately from the catheter shaft assembly.

17 Claims, 20 Drawing Sheets

U.S. PATENT DOCUMENTS

| | | | |
|---|---|---|---|
| 4,815,449 A | | 3/1989 | Horowitz |
| 4,861,520 A | | 8/1989 | Van't Hooft et al. |
| 4,900,314 A | * | 2/1990 | Quackenbush ............... 604/45 |
| 4,936,823 A | | 6/1990 | Colvin et al. |
| 4,940,064 A | | 7/1990 | Desai |
| 4,969,863 A | | 11/1990 | Van't Hooft et al. |
| 4,976,720 A | | 12/1990 | Machold et al. |
| 4,983,167 A | | 1/1991 | Sahota |
| 4,994,560 A | | 2/1991 | Kruper, Jr. et al. |
| 4,998,917 A | | 3/1991 | Gaiser et al. |
| 5,002,560 A | | 3/1991 | Machold et al. |
| 5,015,230 A | | 5/1991 | Martin et al. |
| 5,019,042 A | | 5/1991 | Sahota |
| 5,032,113 A | | 7/1991 | Burns |
| 5,034,001 A | | 7/1991 | Garrison et al. |
| 5,040,543 A | | 8/1991 | Badera et al. |
| 5,046,503 A | | 9/1991 | Schneiderman |
| 5,059,166 A | | 10/1991 | Fischell et al. |
| 5,061,273 A | | 10/1991 | Yock |
| 5,063,018 A | * | 11/1991 | Fontirroche et al. ... 156/244.13 |
| 5,084,002 A | | 1/1992 | Liprie |
| 5,087,246 A | | 2/1992 | Smith |
| 5,100,429 A | | 3/1992 | Sinofsky et al. |
| 5,133,956 A | | 7/1992 | Garlich et al. |
| 5,137,513 A | | 8/1992 | McInnes et al. |
| 5,151,149 A | | 9/1992 | Swartz |
| 5,176,617 A | | 1/1993 | Fischell et al. |
| 5,176,661 A | | 1/1993 | Evard et al. |
| 5,180,368 A | | 1/1993 | Garrison |
| 5,195,971 A | | 3/1993 | Sirhan |
| 5,199,939 A | | 4/1993 | Dake et al. |
| 5,213,561 A | | 5/1993 | Weinstein et al. |
| 5,226,889 A | | 7/1993 | Sheiban |
| 5,242,396 A | | 9/1993 | Evard |
| 5,258,419 A | | 11/1993 | Rolando et al. |
| 5,263,963 A | | 11/1993 | Garrison et al. |
| 5,267,960 A | | 12/1993 | Hayman et al. |
| 5,273,738 A | | 12/1993 | Matthews et al. |
| 5,279,562 A | | 1/1994 | Sirhan et al. |
| 5,282,781 A | | 2/1994 | Liprie |
| 5,295,959 A | | 3/1994 | Gurbel et al. |
| 5,295,960 A | | 3/1994 | Aliahmad et al. |
| 5,295,995 A | | 3/1994 | Kleiman |
| 5,300,281 A | | 4/1994 | McMillan et al. |
| 5,302,168 A | | 4/1994 | Hess |
| 5,306,246 A | | 4/1994 | Sahatjian et al. |
| 5,308,356 A | | 5/1994 | Blackshear, Jr. et al. |
| 5,320,824 A | | 6/1994 | Brodack et al. |
| 5,334,154 A | | 8/1994 | Samson et al. |
| 5,336,518 A | | 8/1994 | Narayanan et al. |
| 5,350,361 A | | 9/1994 | Tsukashima et al. |
| 5,352,199 A | | 10/1994 | Tower |
| 5,354,257 A | | 10/1994 | Roubin et al. |
| 5,374,245 A | * | 12/1994 | Mahurkar .................... 604/43 |
| 5,380,747 A | | 1/1995 | Medford et al. |
| 5,395,333 A | | 3/1995 | Brill |
| 5,405,622 A | | 4/1995 | Vernice et al. |
| 5,409,495 A | | 4/1995 | Osborn |
| 5,411,466 A | | 5/1995 | Hess |
| 5,415,664 A | | 5/1995 | Pinchuk |
| 5,425,710 A | | 6/1995 | Khair et al. |
| 5,441,516 A | | 8/1995 | Wang et al. |
| 5,447,497 A | | 9/1995 | Sogard et al. |
| 5,456,667 A | | 10/1995 | Ham et al. |
| 5,458,572 A | | 10/1995 | Campbell et al. |
| 5,484,384 A | | 1/1996 | Fearnot |
| 5,498,227 A | | 3/1996 | Mawad |
| 5,501,667 A | | 3/1996 | Verduin, Jr. |
| 5,501,759 A | | 3/1996 | Forman |
| 5,503,613 A | | 4/1996 | Weinberger |
| 5,503,614 A | | 4/1996 | Liprie |
| 5,507,301 A | | 4/1996 | Wasicek et al. |
| 5,507,769 A | | 4/1996 | Marin et al. |
| 5,516,336 A | | 5/1996 | McInnes et al. |
| 5,538,510 A | * | 7/1996 | Fontirroche et al. ........ 604/265 |
| 5,540,659 A | | 7/1996 | Teirstein |
| 5,542,925 A | | 8/1996 | Orth |
| 5,549,552 A | | 8/1996 | Peters et al. |
| 5,573,508 A | | 11/1996 | Thornton |
| 5,573,509 A | | 11/1996 | Thornton |
| 5,599,306 A | | 2/1997 | Klein et al. |
| 5,616,114 A | | 4/1997 | Thornton et al. |
| 5,618,266 A | | 4/1997 | Liprie |
| 5,643,171 A | | 7/1997 | Bradshaw et al. |
| 5,645,529 A | | 7/1997 | Fagan et al. |
| 5,653,691 A | | 8/1997 | Rupp et al. |
| 5,658,311 A | | 8/1997 | Baden |
| 5,683,345 A | | 11/1997 | Waksman et al. |
| 5,688,486 A | | 11/1997 | Watson et al. |
| 5,707,332 A | | 1/1998 | Weinberger |
| 5,730,698 A | | 3/1998 | Fischell et al. |
| 5,738,901 A | | 4/1998 | Wang et al. |
| 5,762,906 A | | 6/1998 | Creighton |
| 5,766,192 A | | 6/1998 | Zacca |
| 5,782,740 A | | 7/1998 | Schneiderman |
| 5,782,742 A | | 7/1998 | Crocker et al. |
| 5,797,869 A | | 8/1998 | Martin et al. |
| 5,797,948 A | | 8/1998 | Dunham |
| 5,826,588 A | | 10/1998 | Forman |
| 5,833,672 A | * | 11/1998 | Kawata et al. ............... 604/523 |
| 5,836,965 A | | 11/1998 | Jendersee et al. |
| 5,840,064 A | | 11/1998 | Liprie |
| 5,840,067 A | | 11/1998 | Berguer et al. |
| 5,851,171 A | | 12/1998 | Gasson |
| 5,863,284 A | | 1/1999 | Klein |
| 5,868,703 A | * | 2/1999 | Bertolero et al. ...... 604/102.01 |
| 5,871,436 A | | 2/1999 | Eury |
| 5,882,290 A | | 3/1999 | Kume |
| 5,882,291 A | | 3/1999 | Bradshaw et al. |
| 5,899,882 A | | 5/1999 | Waksman et al. |
| 5,910,101 A | | 6/1999 | Andrews et al. |
| 5,938,582 A | | 8/1999 | Ciamacco, Jr. et al. |
| 5,947,924 A | | 9/1999 | Liprie |
| 5,951,458 A | | 9/1999 | Hastings et al. |
| 5,954,741 A | | 9/1999 | Fox |
| 5,961,765 A | | 10/1999 | Kastenhofer |
| 5,964,730 A | | 10/1999 | Williams et al. |
| 5,976,106 A | | 11/1999 | Verin et al. |
| 5,984,963 A | | 11/1999 | Ryan et al. |
| 6,117,064 A | | 10/2000 | Apple et al. |
| 6,190,356 B1 | | 2/2001 | Bersin |
| 6,196,996 B1 | | 3/2001 | Teirstein \ |

FOREIGN PATENT DOCUMENTS

| | | |
|---|---|---|
| EP | 0633041 A1 | 7/1993 |
| EP | 0688580 A1 | 6/1994 |
| EP | 0801961 A2 | 4/1997 |
| EP | 0829271 A2 | 9/1997 |
| EP | 0865803 A2 | 3/1998 |
| EP | 0879614 A1 | 5/1998 |
| WO | WO 92/17236 | 3/1992 |
| WO | WO 93/04735 | 9/1992 |
| WO | wo 94/25106 | 5/1994 |
| WO | WO 95/19807 | 1/1995 |
| WO | WO 95/26681 | 3/1995 |
| WO | WO 96/06654 | 8/1995 |
| WO | WO 96/10436 | 9/1995 |
| WO | WO 96/14898 | 11/1995 |
| WO | WO 96/19255 | 12/1995 |
| WO | WO 97/07740 | 8/1996 |
| WO | WO 97/37715 | 4/1997 |

| | | |
|---|---|---|
| WO | WO 97/40889 | 4/1997 |
| WO | WO 98/01182 | 5/1997 |
| WO | WO 98/01183 | 7/1997 |
| WO | WO 98/01184 | 7/1997 |
| WO | WO 98/01185 | 7/1997 |
| WO | WO 98/39052 | 1/1998 |

OTHER PUBLICATIONS

–Meyer Friedman et al., "The Antiatherogenic Effect of Iridium$^{192}$ Upon the Cholesterol–Fed Rabbit", *Journal of Clinical Investigation*, vol. 43, No. 2, pp. 185–192, 1964.

–Meyer Friedman et al., "Effect of Iridium$^{192}$ Radiation on Thromboatherosclerotic Plaque in the Rabbit Aorta", *Arch Path*, vol. 80, pp 285–290, Sep. 1965.

–Paul Jack Hoopes, D.V.M., Ph.D. et al., "Intraoperative Irradiation of the Canine Abdominal Aorta and Vena Cava", *Int. J. Radiation Oncology Biol. Phys.*, vol. 13, pp 715–722, May 1987.

–John T. Dawson, Jr, M.D., "Theoretic Considerations Regarding Low–Dose Radiation Therapy", Texas Heart Institute Journal, vol. 18, No. 1, pp 4–7, 1991.

–Robert S. Schwartz, M.D. et al. "Effect of External Beam Irradiation on Neointimal Hyperplasia After Experimental Coronary Artery Injury", *JACC*, vol. 19, No. 5, pp 1106–1113, Apr. 1992.

–Joseph G. Wiedermann, M.D. et al., "Intracoronary Irradiation Markedly Reduces Restenosis After Balloon Angioplasty in a Porcine Model", *JACC*, vol. 23, No. 6, pp 1491–1498, May 1994.

–Tim A. Fischell, M.D. et al., "Low–Dose B–Particle Emission from 'Stent' Wire Results in Complete, Localized Inhibition of Smooth Muscle Cell Proliferation", *Circulation*, vol. 90, No. 6, pp 2956–2963, Dec. 1994.

Maria G. M. Hunink, M.D. et al., "Risks and Benefits of Femoropopliteal Percutaneous Balloon Angiplasty", *Journal of Vascular Surgery*, vol. 17, No. 1, pp 183–194, Jan. 1993.

–Ron Waksman M.D. et al., "Endovascular Low–Dose Irradiation Inhibits Neointima Formation After Coronary Artery Balloon Injury in Swine", *Circulation*, vol. 91, No. 5, pp 1533–1539, Mar. 1, 1995.

–Z. Weshler et al., "Inhibition by Irradiation of Smooth Muscle Cell Proliferation in the De–Endothelialized Rat Aorta", *Frontiers in Radiation Biology*, pp 133–138, Oct. 1988.

–C. Hehrlein et al. "Radioactive Stents", *Discoveries in Radiation for Restenosis*, Abstract 22, pp 63–64, Jan. 1996.

–Tim A. Fischell, M.D. et al., "A Beta–Particle Emitting Radioisotope Stent for The Prevention of Restenosis," *Discoveries in Radiation for Restenosis*, Abstract 23, p 65, Jan. 1996.

–Alexander N. LI et al., "A Novel Brachyehtapy Source for Treatment of Coronary Artery Restenosis," *Discoveries in Radiation for Restenosis*, Abstract 24, pp 67–72, Jan. 1996.

–Ron Waksman, M.D., "Catheter–Based Radiation In Stented Arteries", *Discoveries in Radiation for Restenosis*, Abstract 25, pp 73–74, Jan. 1996.

–Louis G. Martin, M.D., "Radiation for Peripheral Applications: Technical Aspects," *Discoveries in Radiation for Restenosis*, Abstract 27, pp 81–82, Jan. 1996.

–Alan B. Lumsden, M.D. et al, "Restenosis in Peripheral Vascular Disease," *Discoveries in Radiation for Restenosis*, Abstract 28, pp 83–88, Jan. 1996.

–B. Schopohl et al., "Endovascular Irradiation for Avoidance or Recurrent Stenosis After Stent Implantation in Peripheral Arteries–5 years Follow–up", *Discoveries in Radiation for Restenosis*, Abstract 29, pp 89–92, Jan. 1996.

–Ron Waksman, M.D., "Radiation in the Peripheral System at Emory," *Discoveries in Radiation for Restenosis*, Abstract 30, pp 93–94, Jan. 1996.

–Paul S. Teirstein et al., "Catheter–Based Radiation Therapy to Inhibit Restenosis Following Coronary Stenting," *Discoveries in Radiation for Restenosis*, Abstract 31, p 99, Jan. 1996.

–Spencer B. King III, M.D., "Clinical Restenosis Trials Using Beta Energy Radiation," *Discoveries in Radiation for Restenosis*, Abstract 32, pp 101–102, Jan. 1996.

–Philip Urban, M.D. et al., "Endovascular Irradiation with 90Y Wire", *Discoveries in Radiation for Restenosis*, Abstract 33, pp 103–104, Jan. 1996.

–Jose A. Condado, et al., "Late Follow–up After Percutaneous Transluminal Coronary Angioplasty (PTCA) and Intracoronary Radiation Therapy (ICRT)," *Discoveries in Radiation for Restenosis*, Abstract 34, p 105, Jan. 1996.

–Thomas D. Weldon, "Catheter Based Beta Radiation System", *Discoveries in Radiation for Restenosis*, Abstract 35, p 111, Jan. 1996.

–Eric Van't Hooft, et al., "HDR Afterloader for Vascular Use", *Discoveries in Radiation for Restenosis*, Abstract 36, p 113, Jan. 1996.

–Robert E. Fischell, et al., "The Radioisotope Stent: Conception and Implementation", *Discoveries in Radiation for Restenosis*, Abstract 37, p 115, Jan. 1996.

–Youri Popowski M.D., et al., "Radioactive Wire in a Self–Centering Catheter System", *Discoveries in Radiation for Restenosis*, Abstract 38, pp 117–118, Jan. 1996.

–Richard V. Calfee, Ph.D., "High Dose Rate Afterloader System For Endovascular Use–Neocardia", *Discoveries in Radiation for Restenosis*, Abstract 39, pp 119, Jan. 1996.

–Dr. Edward F. Smith III, "Issues on Handling Radioactive Devices to Prevent Restenosis", , *Discoveries in Radiation for Restenosis*, Abstract 40, pp 121–122, Jan. 1996.

–Richard E. Kunts, M.D. et al., "Generalized Model of Restenosis After Conventional Balloon Angioplasty, Stenting and Directional Atherectomy", *JACC*, vol. 21, No. 1, pp 15–25, Jan. 1993.

–Robert S. Schwartz et al., "Differential Neointimal Response to Coronary Artery Injury in Pigs and Dogs", *Arteriosclerosis and Thrombosis*, vol. 14, No. 3, pp 395–400, Mar. 1994.

–Michael Haude, M.D. et al, "Quantitative Analysis of Elastic Recoil after Balloon Angioplasty and After Intracoronary Implantation of Balloon–Expandable Palmaz–Schatz Stents", *JACC*, vol. 21, No. 1, pp 26–34, Jan. 1993.

William S. Wientraub M.D. et al., "Can Restenosis After Coronary Angiplasty Be Predicted From Clinical Variables?", *JACC*, vol. 21, No. 1, pp 6–14, Jan. 1993.

–Tsunekazu Kakuta, M.D. et al., "Differences in Compensatory Vessel Enlargement, Not Intimal Formation, Account for Restenosis After Angioplasty in the Hypercholesterolemic Rabbit Model," *Circulation*, vol. 89, No. 6, pp 2809–2815, Jun. 1994.

–Christina Unterberg, M.D. et al., "Reduced Acute Thrombus Formation Results in Decreased Neointimal Proliferation After Coronary Angioplasty", *JACC*, vol. 26, No. 7, pp 1747–1754, Dec. 1995.

Lewis W. Johnson et al., "Review of Radiation Safety in the Cardiac Catheterization Laboratory", *Catheterization and Cardiovascular Diagnosis*, vol. 25, pp 186–194, 1992.

–Roger W. Byhardt et al., "The Heart and Blood Vessels", *Radiation Oncology Rationale, Technique, Results*, pp 277–284, Jan. 1996.

–C.G. Soares et al., "Measurement of Radial Dose Distributions Around Small Beta Particle Emitters Using High Resolution Radiochromic Foil Dosimetry", *Nuclear Technology Publishing*, vol. 4, No. 1, pp 367–372, 1992.

Louis K. Wagner, PH.D. et al., "Potential Biological Effects Following High X–Ray Dose Interventional Procedures", *Journal of Vascular and Interventional Radiology*, pp 71–84, Jan.–Feb. 1994.

–Ron Waksman M.D. et al., "Intracoronary Low–Dose B–Irradiation Inhibits Neointima Formation After Coronary Artery Balloon Injury in the Swine Restenosis Model", *Circulation*, vol. 92, No. 10, pp 3025–3031, Nov. 15, 1995.

–Joseph G. Wiedermann, M.D. et al., "Intracoronary Irradiation Markedly Reduces Neointimal Proliferation After Balloon Angioplasty in Swine: Persistent Benefit at 6–month Follow–up", *JACC* vol. 25, No. 1, pp 1451–1456, May 1995.

–Dieter Liermann et al., "Prophylactic Endovascular Radiotherapy to Prevent Intimal Hyperplasia After Stent Implantation in Femoropoliteal Arteries", *Cardiovascular and Interventional Radiology*, vol. 17, pp 12–16, 1994.

–Joseph G. Widermann et al., "Effects of High–Dose Intracoronary Irradiation on Vasomotor Function and Smooth Muscle Histopathology", *Intracoronary Irradiation and Vasomotion*, pp H125–H132, 1994.

Keith L. March, M.D. et al., "8–Methoxypsoralen and Longwave Ultraviolet Irradiation Are a Novel Antiproliferative Combination for Vascular Smooth Muscle", *Circulation*, vol. 87, No. 1, pp 184–191, Jan. 1993.

–Barry T. Katzen, M.D., "Mechanical Approaches to Restenosis in the Peripheral Circulation", Jan. 1996.

–Vitali Verin, M.D., et al., "Intra–Arterial Beta Irradiation Prevents Neointimal Hyperplasia in a Hypercholesterolemic Rabbit Restenosis Model", *Circulation*, vol. 92, No. 8, pp 2284–2290, Oct. 15, 1995.

–Ron Waksman M.D. et al., "Intracoronary Radiation Before Stent Implantation Inhibits Neointima Formation in Stented Porcine Coronary Arteries", *Circulation*, vol. 92, No. 6, pp 1383–1386, Sep. 15, 1995.

Chrisoph Hehrlein, M.D., et al., "Low–Dose Radioactive Endovascular Stents Prevent Smooth Muscle Cell Proliferation and Noeintimal Hyperplasia in Rabbits", *Circulation*, vol. 92, No. 6, pp 1570–1575, Sep. 15, 1995.

–PCT Search Report PCT/US 99/03327 mailed Jun. 18, 1999.

–PCT Search Report PCT/US 99/03343 mailed Jun. 17, 1999.

PCT Search Report PCT/US 99/03328 mailed Jun. 18, 1999.

PCT Search Report PCT/US 99/03329 mailed Jun. 18, 1999.

PCT Search Report PCT/US 99/03360 mailed Jun. 17, 1999.

\* cited by examiner

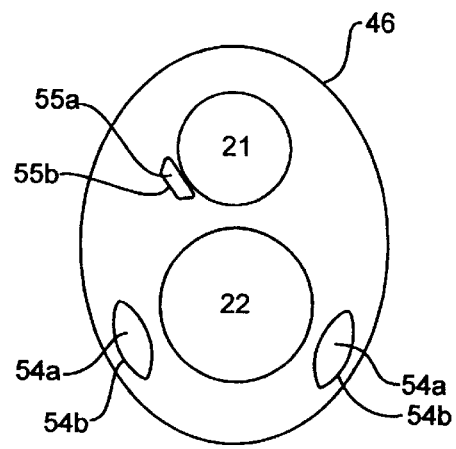
FIG. 20a
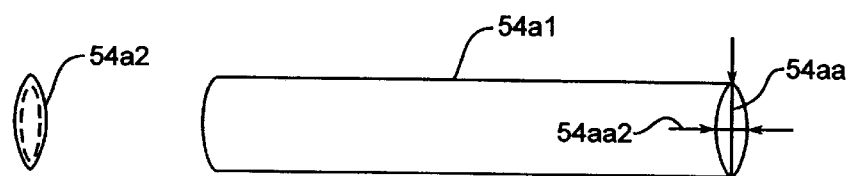
FIG. 20d
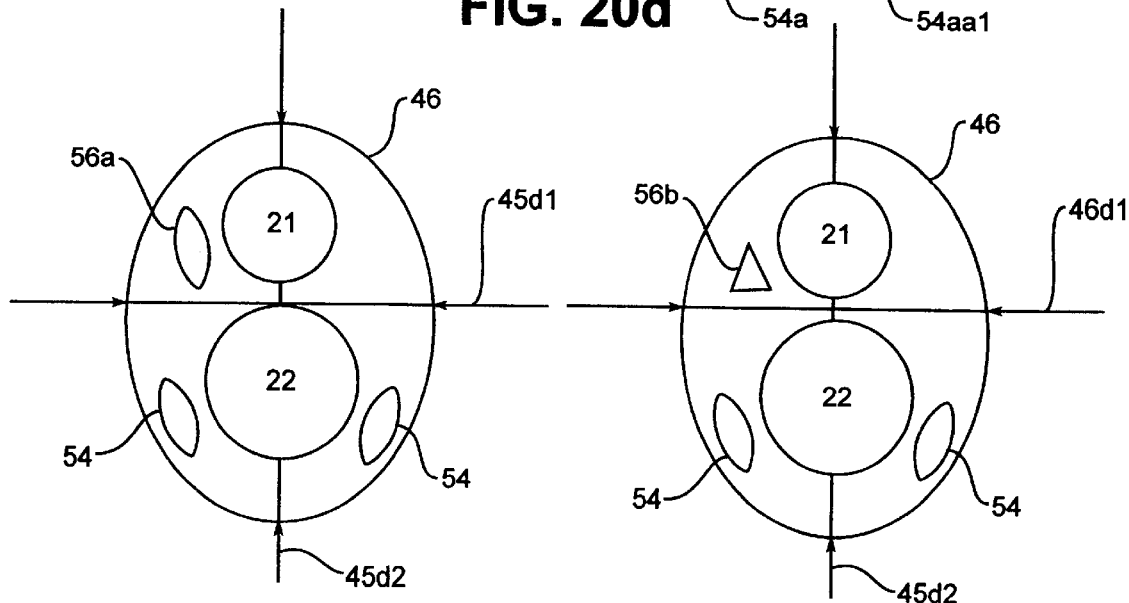
FIG. 20b  FIG. 20c

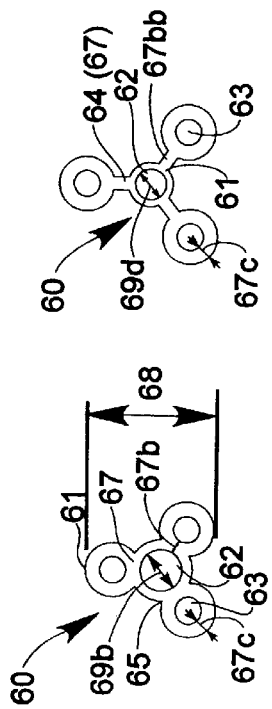
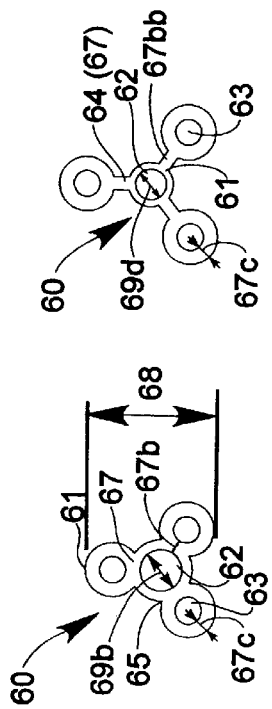
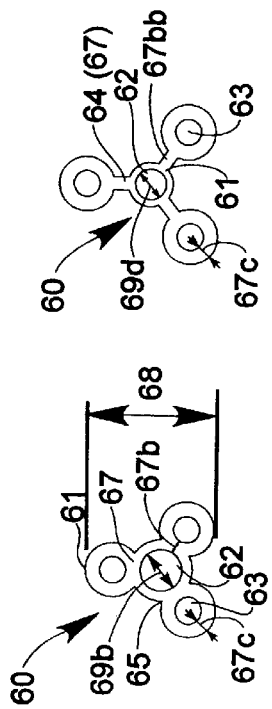
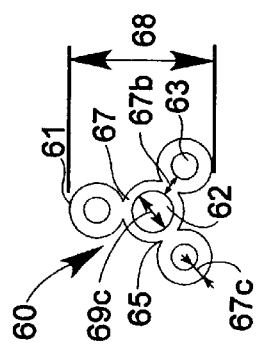
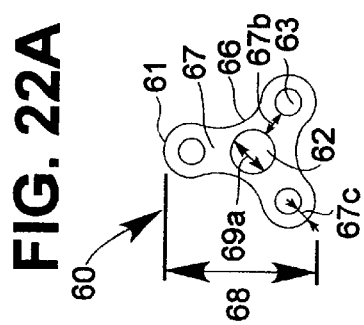
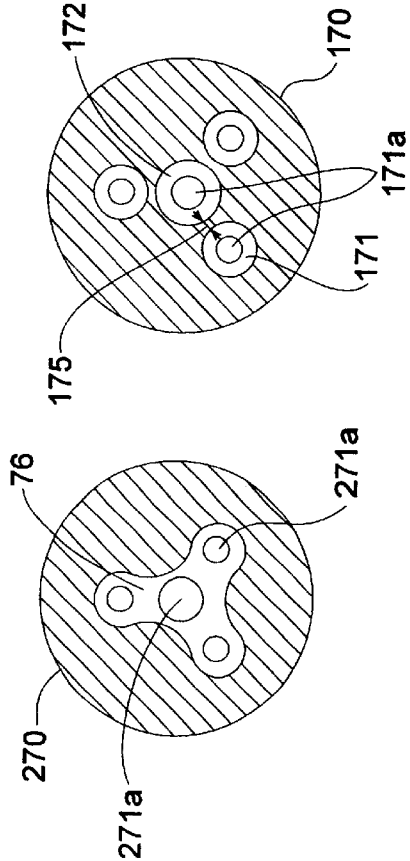

C-C

B-B

A-A

MULTI-LUMEN EXTRUSION TUBING

BACKGROUND OF THE INVENTION

1. Field of the Invention

The present invention relates to medical catheters and more particularly to a multi-lumen balloon for a radiation centering catheter.

2. Description of Related Art

Medical catheters generally include elongate tube-like members that may be inserted into the body, either percutaneously or via a body orifice, for any of a wide variety of diagnostic and interventional purposes. Such catheters are particularly useful with regard to certain cardiovascular applications where the object is to deliver a treatment or instrument to a remote lesion.

Percutaneous Transluminal Coronary Angioplasty (PTCA or balloon angioplasty) is the predominant treatment for coronary vessel stenosis. In PTCA, catheters are inserted into the cardiovascular system via the femoral artery under local anesthesia. A pre-shaped guiding catheter is positioned in the coronary artery, and a dilatation catheter having a distensible balloon portion is advanced through the guiding catheter into the branches of the coronary artery until the balloon portion traverses or crosses a stenotic lesion. The balloon portion is then inflated with a medium to compress the atherosclerosis in a direction generally perpendicular to the wall of the artery, thus dilating the lumen of the artery. Patients treated by PTCA procedures, however, suffer from a high incidence of restenosis, i.e., the same area of the coronary vessel collapses or becomes obstructed.

Recent preclinical and early clinical studies indicate that intervascular radiation after balloon angioplasty can reduce the rate of restenosis caused by intimal hyperplasia. Generally, in an intervascular radiotherapy procedure, a flexible catheter is inserted into the cardiovascular system of a patient and then advanced to the region of the vessel that has been subjected to the angioplasty procedure. A radiation source or a treatment catheter having a radiation source inside it is then advanced through the flexible catheter so that the radiation source reaches the stenosed vascular site and can deliver an effective dose of radiation. After the radiation treatment, the catheter and radiation source are removed.

Because for a given radiation source activity, the intensity of the radiation delivered to a vessel wall varies in inverse proportion to the square of the distance between the radiation source and the vessel wall, it is desirable to hold the radiation source at, or reasonably near, the center of the vessel for a given treatment period. If the source is not centered within vessel, the vessel wall nearest the source may receive an excess of radiation, while the portion of the vessel wall farthest from the source may be underexposed to the radiation.

There are a number of ways to center a radiation source within a vessel. One such way is using a spiral balloon having a central lumen in which the radiation source is advanced to the stenosed vessel site. In a spiral balloon catheter, the balloon is wrapped or molded in a spiral fashion around a flexible centering lumen. When inflated, the balloon outer diameter pushes against the vessel walls while the inner balloon diameter pushes the radiation source lumen toward the center of the vessel.

Spiral balloons have several significant drawbacks when used in intervascular radiotherapy to control restenosis. The first drawback is that because the balloon is wrapped or molded in a spiral shape around the centering lumen of the catheter, the centering effect of the radiation source decreases as the pitch of the turns of the spiral balloon increases. Thus, the fewer turns a spiral balloon has in its configuration, the less centered the radiation source is inside the vessel. Also, if the spiral balloon is over-pressurized, it will lose its spiral shape, thus leading to inconsistent centering of the radiation source. Another drawback with a spiral balloon is that because every spiral is a taper, when the balloon is in a deflated configuration, it creates a stiff catheter with a bulky balloon. This leads to poor access and limits the use of spiral catheters to certain portions of the vascular system. Furthermore, at the end of the intervascular radiation procedure, the tapers create poor refold of the spiral thus making the removal of the balloon catheter difficult for the physician. Another significant disadvantage of using a spiral balloon in intervascular radiation is the spiral balloon's inconsistent blood perfusion ability. Good blood perfusion of the vessel is achieved only when the blood is flowing freely through the spiral cavity created by the balloon. If any portion of the spiral cavity is blocked, then the flow of the blood is also stopped at that point. Thus, blood perfusion may not be adequate.

Another way to center a radiation source within a vessel is to use a segmented balloon catheter having a series of peaks and valleys created by segmenting an ordinary balloon catheter. The segmented balloon centers the centering lumen using the same principle as the spiral balloon catheter.

An additional way to center a radiation source within a vessel is by using a catheter having an outer balloon and an inner balloon disposed within the outer balloon. Generally, the inner and outer balloons are positioned parallel to each other and axially with the catheter shaft. The inner and outer balloons may have a spiral or a segmented configuration. The inner centering balloon may also be a multiple axial lumen balloon, where the lumens extend parallel to the catheter shaft.

Another way to center a radiation source within a vessel is by having a balloon attached to the distal portion of a radioguide catheter. When inflated, the balloon engages the walls of the vessel to center the treatment channel. The balloon may also be configured to include spiral lumens or/and perfusion lumens to permit perfusion of the blood when the balloon is inflated.

Segmented balloon catheters and multiple balloon catheters have many of the same drawbacks as those associated with spiral balloon catheters, including inadequate centering of the radiation source, poor balloon refold, catheter stiffness, bulky balloon configuration, inconsistent perfusion, etc. While balloons configured with spiral lumens or perfusion lumens have a better perfusion capability than single-spiral, segmented, or multiple balloon configurations, they still have some disadvantages, including poor balloon foldability, catheter stiffness, and less than optimal perfusion capability.

Currently, most radioguide centering catheters used in the industry are of the type known in the industry as "tip RX" (RX being "rapid exchange"). Tip RX radioguide centering catheters are characterized by a short guidewire riding length of approximately 5 mm and a guidewire exit notch distal to the centering balloon. Tip RX catheter assemblies have several disadvantages when used in vascular radiation therapy. First, the trackability of the catheter is not consistent in a challenging vascular anatomy, and can go from excellent to poor for no apparent reason. Poor catheter trackability may make it impossible to place the catheter at the desired treatment site, preventing delivery of the radiation therapy. Pushability is similarly problematic with the tip RX catheter. When withdrawing a tip RX catheter, it is also possible to prolapse the guidewire, complicating the procedure. Another disadvantage is that because the guidewire lumen is distal to the balloon, it adds approximately 10 mm to the overall length of the tip. Cardiologists however, prefer to have the tip of the catheter as short as possible in order to prevent potential injury to the artery distal to the treatment site. Another disadvantage of using a tip RX balloon catheter for vascular radiation therapy is that since the exit notch is distal to the balloon, the guidewire must be left in place, thus creating a small but measurable shadow in the radiation dosimetry.

In addition to tip RX balloon catheters, other catheter designs used for vascular radiotherapy employ an "over-the-wire" ("OTW") guidewire lumen configuration. Currently, these OTW radiation delivery catheters do not provide the capability of centering the radiation source. Furthermore, while an over-the-wire configuration catheter assembly allows for the guidewire to be pulled back during radiation delivery, the guidewire lumen shifts the source away from the center of the catheter, thus making the centering of the radiation source even more problematic.

The manufacture of inflated balloons with diameters in a range of approximately 1.0 to 6.0 millimeters (mm) presents another significant issue with current balloon catheter designs. One of the challenges relates to the stiffness of the balloon. For example, some manufacturers have used several separate small diameter balloons and attached them using glue or other bonding material around a central catheter shaft to form a balloon catheter. Because the glue or bonding material is positioned along the catheter shaft, the catheter is stiff and difficult to use in coronary vessels having tortuous paths. Therefore, this design configuration gives sub-par performance. Others have used an extrusion process to manufacture a multiple balloon radiation centering catheter. During the extrusion process, however, excess material is generated which tends to make the catheter stiff. In addition, because the material used for the radiation source lumen has generally been different than the material used for the guidewire lumen or the centering balloons, the extrusion process is extremely difficult to complete successfully.

SUMMARY OF THE INVENTION

A multi-lumen tubing and method of manufacturing the same is described. The multi-lumen tubing includes a tubing body having a central lumen and a plurality of outer lumens disposed around the central lumen. The plurality of outer lumens are coupled with the central lumen by a shared wall. The multi-lumen tubing also includes an undercut region disposed the central lumen and the plurality of outer lumens.

BRIEF DESCRIPTION OF THE DRAWINGS

The present invention is illustrated by way of example and not limitation in the accompanying figures:

FIG. 20a is a cross-sectional view of a configuration for a completed balloon proximal seal for a four-lumen balloon.

FIG. 20b is a cross-sectional view of a second configuration for a completed balloon proximal seal for a four-lumen balloon.

FIG. 20c is a cross-sectional view of a third configuration for a completed balloon proximal seal for a four-lumen balloon.

FIG. 20d is a side view of a "football-shape" cross section mandrel used to perform the proximal seal for a multi-lumen balloon.

FIG. 22a is a cross-sectional view of a basic four-lumen (quad-lumen) extrusion tubing with "shared wall" and "fillet radius" regions.

FIG. 22b is a cross-sectional view of a tip and die assembly used to make the quad-lumen extrusion tubing of FIG. 22a.

FIG. 23a is a cross-sectional view of a second embodiment of a quad-lumen extrusion tubing with "shared wall" and "undercut" regions.

FIG. 23b is a cross-sectional view of a tip and die assembly used to make the quad-lumen extrusion tubing of FIG. 23a.

FIG. 24a is a cross-sectional view of a third embodiment of a quad-lumen extrusion tubing with "shared wall" and "undercut" regions.

FIG. 24b is a cross-sectional view of a tip and die assembly used to make the quad-lumen extrusion tubing of FIG. 24a.

FIG. 25a is a cross-sectional view of a fourth embodiment of a quad-lumen extrusion tubing with "standoffs" regions.

FIG. 25b is a cross-sectional view of a tip and die assembly used to make the quad-lumen extrusion tubing of FIG. 25a.

DETAILED DESCRIPTION OF THE INVENTION

A multi-lumen balloon for use in a fluted balloon centering catheter and method for providing the same is described. The present invention is a multi-lumen balloon for a radiation centering catheter that maintains a radiation source at the center of a cardiovascular artery, has improved blood perfusion capability, and has improved balloon refolding characteristics. The present invention also provides an improved method of manufacture for a multi-lumen balloon design for a radiation centering catheter, where such method allows the manufacture of the multi-lumen balloon sub-assembly to be done separately from the catheter shaft assembly. Furthermore, the present invention is a multi-lumen balloon centering catheter assembly with an improved guidewire design and method for providing the same. In addition, the present invention provides improved proximal and distal balloon seal designs and method of manufacture for the same.

Figure 1:
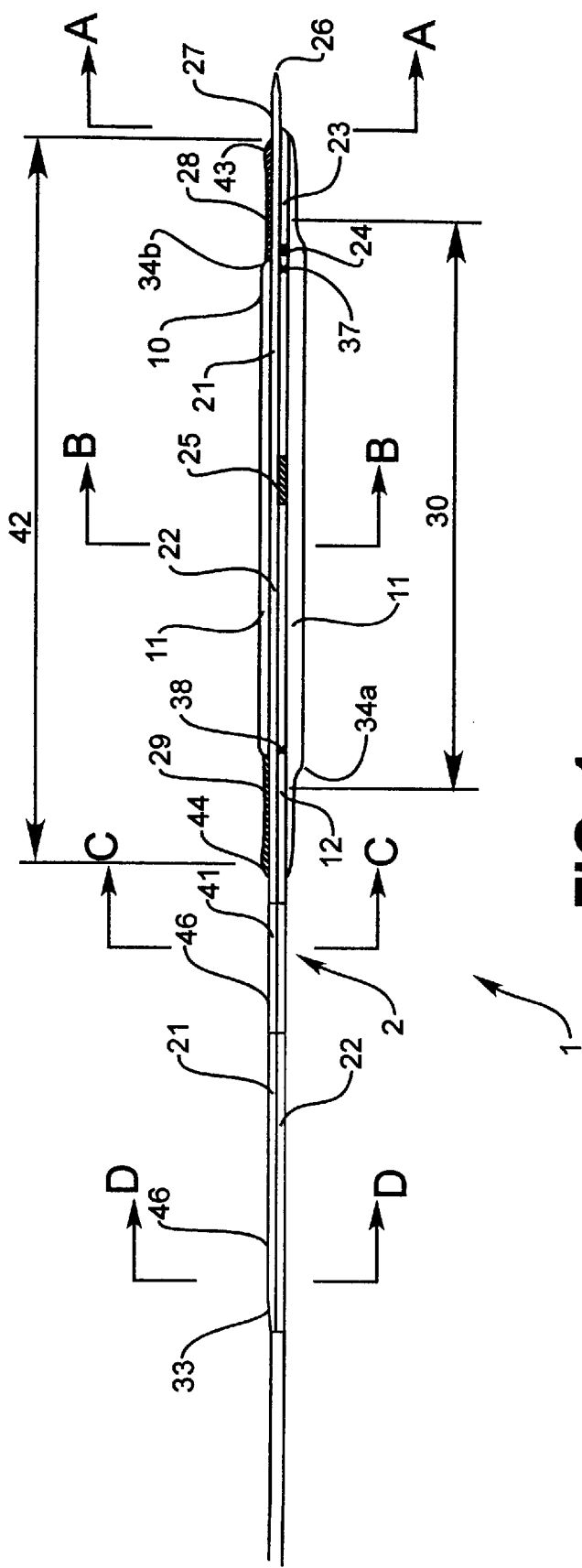
FIG. 1 is a side view of one embodiment of a multi-lumen fluted balloon catheter assembly for centering a radiation source, with guidewire lumen extending through one of the outer lumens of the balloon.
Figure 2:
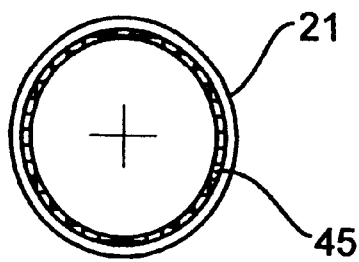
FIG. 2 is a cross-sectional view of the multi-lumen fluted balloon catheter assembly of FIG. 1 taken along line A—A.

In the following detailed description, numerous specific details are set forth in order to provide a more thorough understanding of the present invention. However, it will be apparent to those skilled in the art to which this invention pertains that the present invention may be practiced without these specific details. In other instances, well-known devices, methods, procedures, and individual components have not been described in detail so as not to unnecessarily obscure aspects of the present invention. The present invention is a multi-lumen fluted balloon radiation centering catheter. FIG. 1 shows an embodiment of the multi-lumen fluted balloon centering catheter assembly 1 of the present invention that includes a multi-lumen balloon 10 and an interventional catheter 2 disposed at the proximal end of the balloon 10.

Balloon 10 includes a central lumen and a plurality of outer lumens (or lobes) disposed around the central lumen. The outer lumens are integrally coupled with the central lumen so as to form the multi-lumen balloon. It should be noted that although the multi-lumen balloon configurations illustrated and discussed hereafter make reference to a four-lumen balloon configuration (i.e., balloon with a central lumen and three outer lumens), the multi-lumen balloon of the present invention is not limited to this four-lumen balloon arrangement. As it will be described in the later sections, for some treatment applications and/or vessel treatment area configurations, using a three-lumen balloon having a central lumen and two outer lumens may be desirable. In addition, for some applications, having a balloon with more than four lumens may be desirable.

The interventional catheter 2 used with the multi-lumen balloon 10 may be one of several configurations known in the art, including a standard Rapid Exchange ("RX") design (as shown in side views in FIGS. 1 and 13) where a guidewire lumen 21 passes through the balloon 10 and exits proximal to the balloon 10; a tip (or distal) RX design (as shown in a side view in FIG. 10) where a short guidewire lumen 21 is provided at a distal tip of the balloon 10; or an over-the-wire ("OTW") design where the guidewire lumen 21 extends the full length of the fluted balloon catheter assembly 1, including the multi-lumen balloon 10 and interventional catheter 2.

Multi-lumen Balloon

Figure 18:
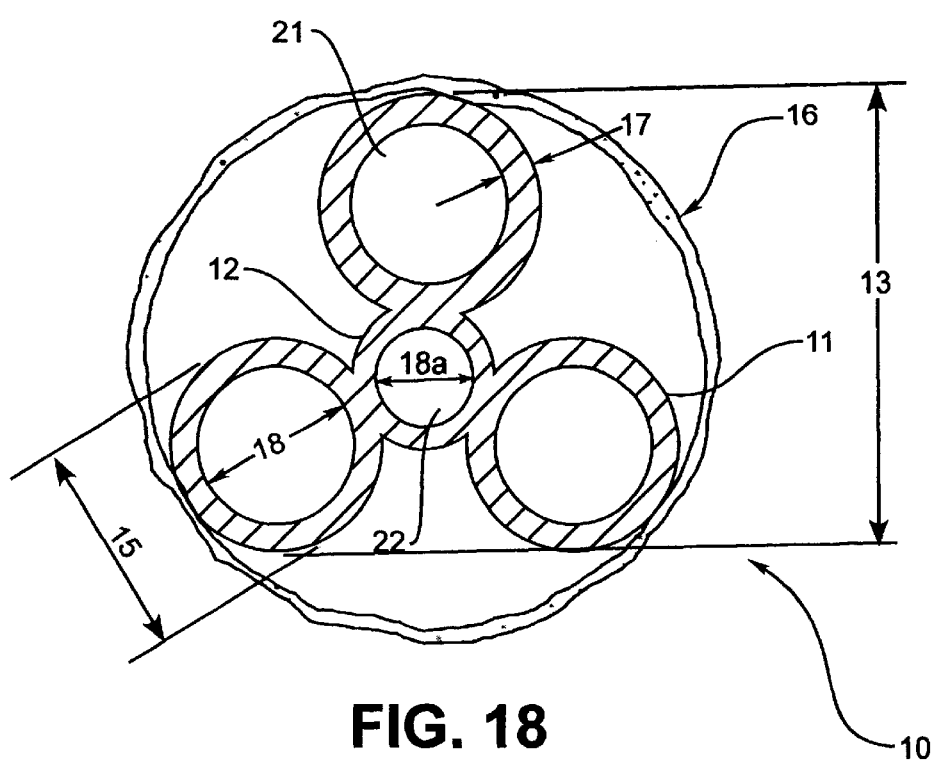
FIG. 18 is a cross-sectional view of a four-lumen balloon for a centering catheter assembly.

Referring to FIG. 18, a cross sectional view of one embodiment of a multi-lumen balloon 10 for treating a body vessel 16 in the vascular system is shown. Balloon 10 includes a central lumen 12 and a plurality of outer lumens (or lobes) 11 disposed around the central lumen 12. The outer lumens 11 are integrally coupled with the central lumen 12 so as to form the multi-lumen balloon 10. Each of the balloon outer lumens 11 has an inner radial length (or diameter) 18 and an outer diameter 15, defining balloon outer lumen walls 17. The walls 17 of balloon outer lumens 11 are made very thin to allow proper inflation and deflation of outer lumens 11. The thickness of the walls 17 ranges from $0.5/1000$ in. to about $3/1000$ in. In one embodiment, wall 17 has a thickness of $0.75/1000$ in.

Figure 3:
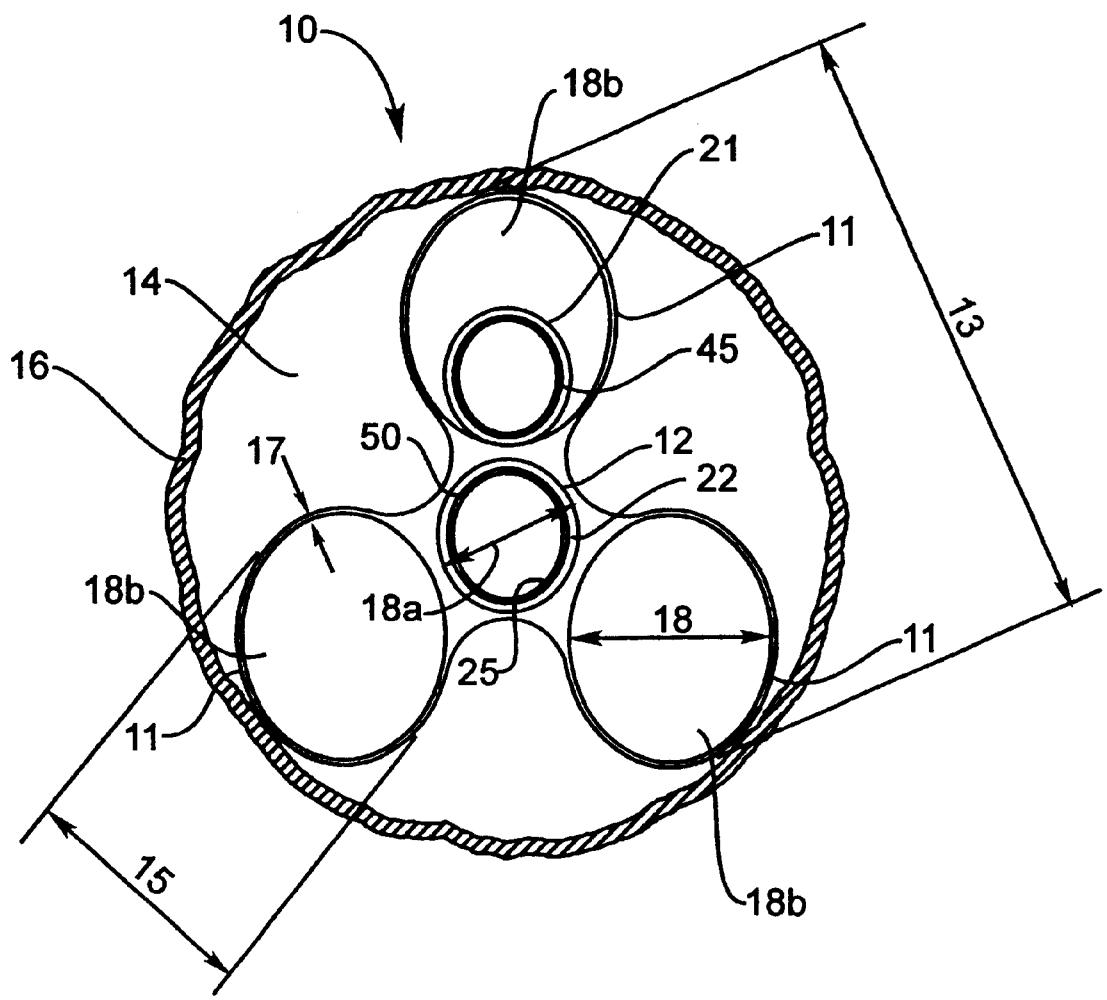
FIG. 3 is a cross-sectional view of the multi-lumen fluted balloon radiation centering catheter assembly of FIG. 1 taken along line B—B.
Figure 11:
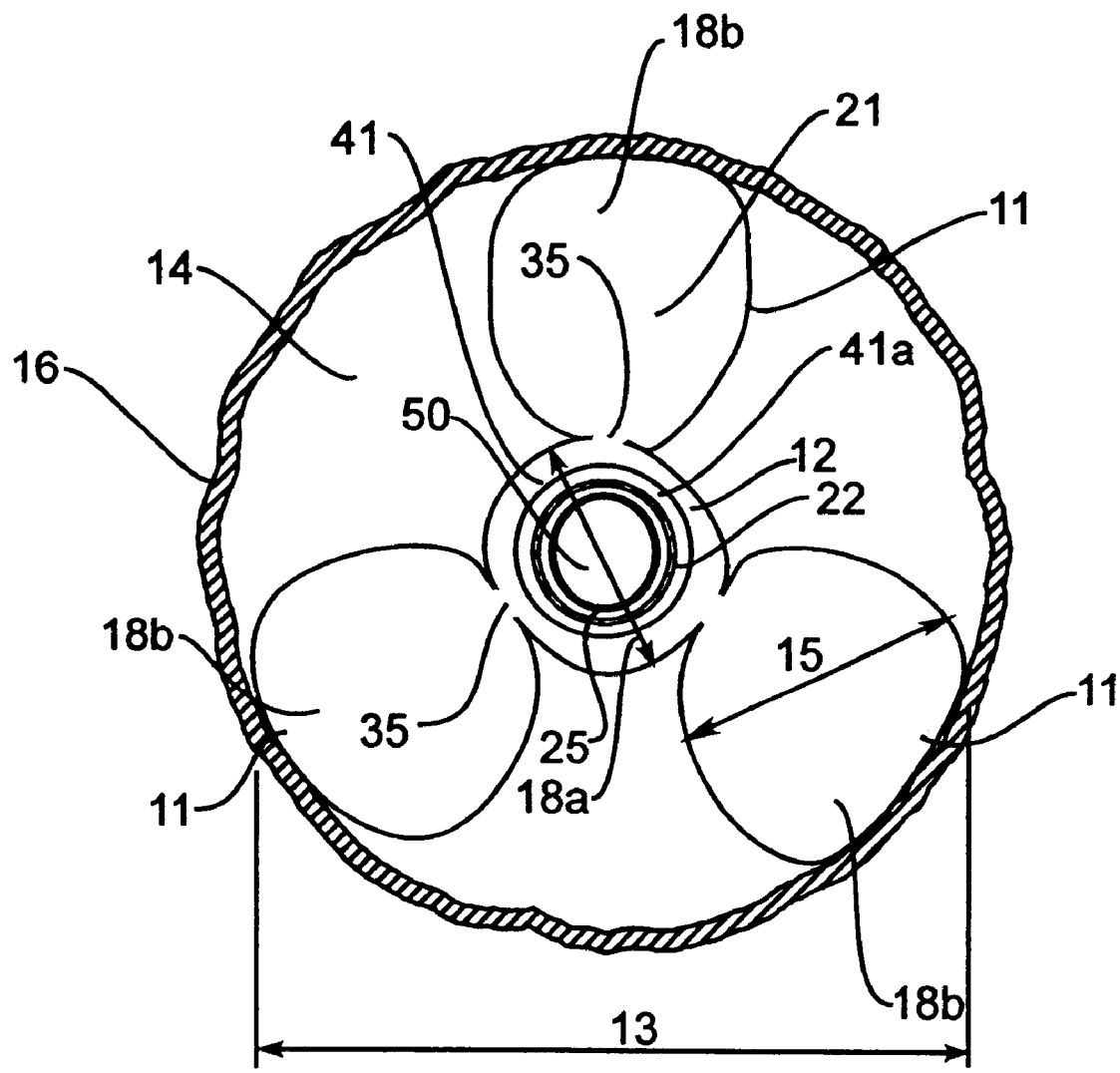
FIG. 11 is a cross-sectional view of the multi-lumen fluted balloon catheter assembly of FIG. 10 taken along line H—H.
Figure 14:
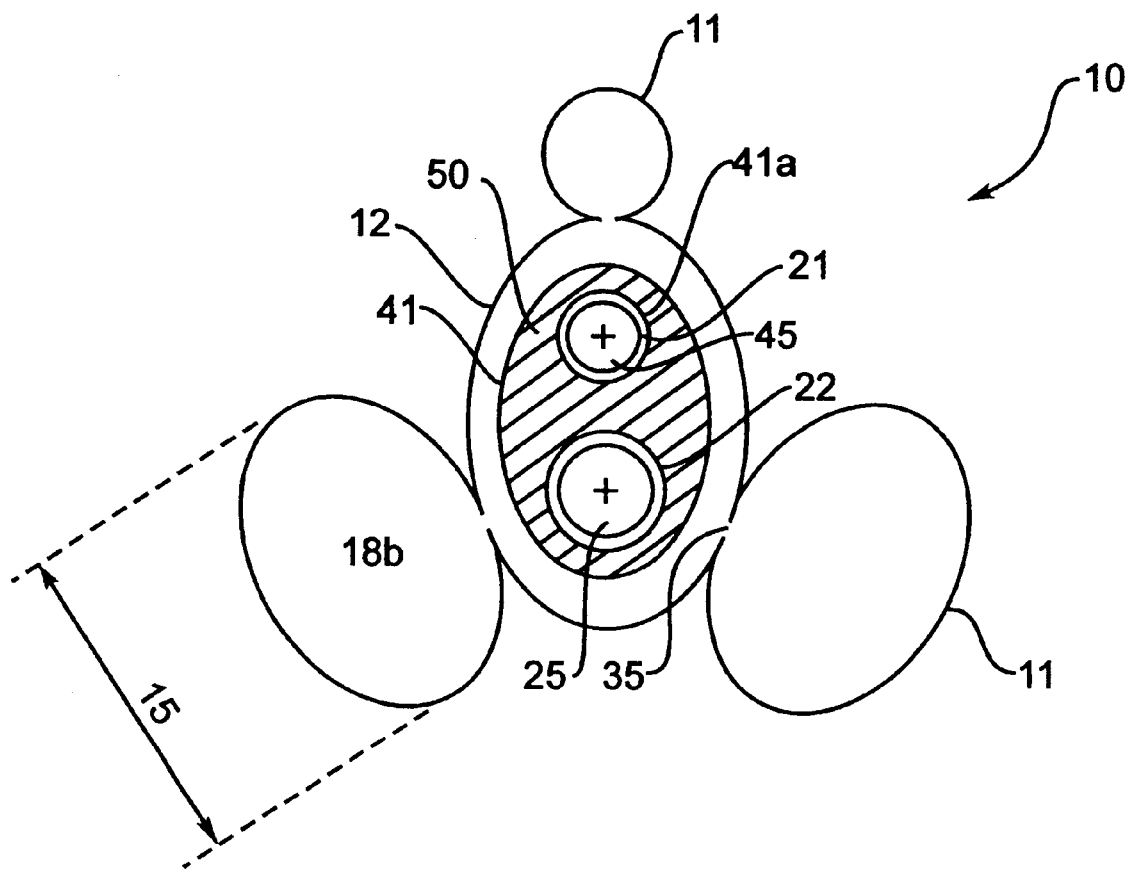
FIG. 14 is a cross-sectional view of the multi-lumen fluted balloon catheter assembly of FIG. 13 taken along line K—K showing a guidewire lumen extending through balloon central lumen.
Figure 15:
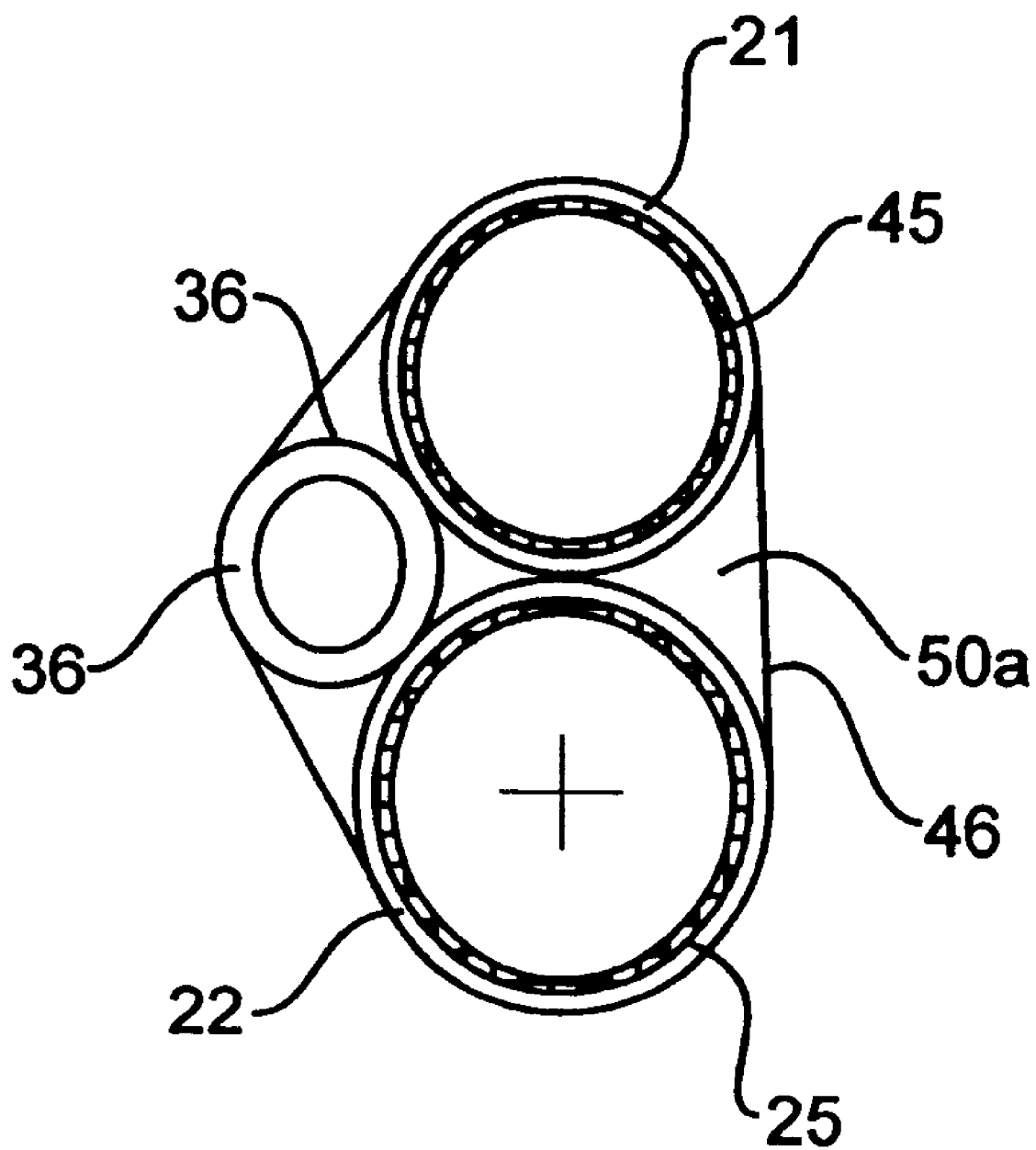
FIG. 15 is a cross-sectional view of the multi-lumen fluted balloon catheter assembly of FIG. 13 taken along line L—L showing guidewire lumen, radiation source lumen, and inflation/deflation lumen within catheter inner member.

The balloon outer lumens 11 can be extruded with either equal diameters 15 (as shown in FIG. 18, and FIGS. 3 and 11) or with unequal (i.e., asymmetrical, lopsided, etc.) diameters 15 (as shown in FIG. 14). The balloon outer lumen has a diameter 15 sized in a range of approximately 0 mm (no balloon lumen) to about 5 mm.

The balloon central lumen 12 has an inner diameter 18a. The central lumen 12 is capable of containing a radiation source (with or without a radiation source lumen) therein. The diameter 18a of the balloon central lumen 12 is sized based on the radiation source outer diameter, for example a radiation source wire having an outer diameter in a range of approximately $10/1000$ in. to $50/1000$ in. It should be noted that the balloon central lumen diameter 18a may be made smaller than $18/1000$ in. for intervascular radiation treatments using radiation sources having a diameter smaller than $10/1000$ in. or for radiation sources having a liquid configuration.

Continuing with reference to FIG. 18, the multi-lumen balloon 10 of the present invention is used in a fluted balloon radiation centering catheter assembly 1 for treating a body vessel 16 in the vascular system. Given the very small diameter of these body vessels 16, the combined balloon diameter 13 (as measured across all balloon outer lumens 11 while balloon is in an inflated or deployed state) is kept in a range of approximately 1.5 mm to 6 mm for coronary vessels and in a range of approximately 3 mm to 12 mm for peripheral vessels. In one embodiment (shown in FIG. 3), the combined diameter 13 is in a range of approximately 1.5 mm to 4 mm.

Referring now to FIG. 3, another embodiment of the multi-lumen balloon of this invention includes a balloon 10 having a central lumen 12 and three outer lumens (or lobes) 11 disposed around the central lumen 12. The outer lumens 11 are integrally coupled with the central lumen 12 so as to form the multi-lumen balloon 10. Balloon 10 has a guidewire lumen 21 extending lengthwise through one of the balloon outer lumens 11. The guidewire lumen 21 is capable of receiving a guidewire 45 for positioning the multi-lumen balloon 10 (and thus the radiation centering catheter 1) within a body vessel 16. The balloon central lumen 12 is capable of containing a radiation source 25 (with or without a radiation source lumen 22) therein. If a radiation source lumen 22 is used with the radiation source 25 in the balloon central lumen 12, the radiation source lumen 22 would extend lengthwise through the central lumen 12.

It should be noted that the multi-lumen balloon embodiment shown in FIG. 3 is also adapted for receiving the guidewire lumen 21 (with a guidewire 45) through its central lumen 12. In this configuration, since the balloon central lumen 12 would contain both a radiation source 25 (with or without a radiation source lumen 22) and a guidewire lumen 21, the central lumen 12 may take an egg-like shape. The inner diameter 18a of the egg-shaped central lumen 12 would be sized based on the diameter of the radiation source 25 (with its radiation source lumen 22 if one is present) and the diameter of the guidewire lumen 21. In this configuration, the diameter 18a of the balloon central lumen 12 is sized based on the radiation source outer diameter, for example a radiation source wire having an outer diameter in a range of approximately $10/1000$ in. to $50/1000$ in., and the guidewire lumen diameter. Thus, the diameter 18a may be in a range of approximately $10/1000$ in. to $75/1000$ in. In one embodiment, the diameter 18a is $62/1000$ in.

Figure 4:
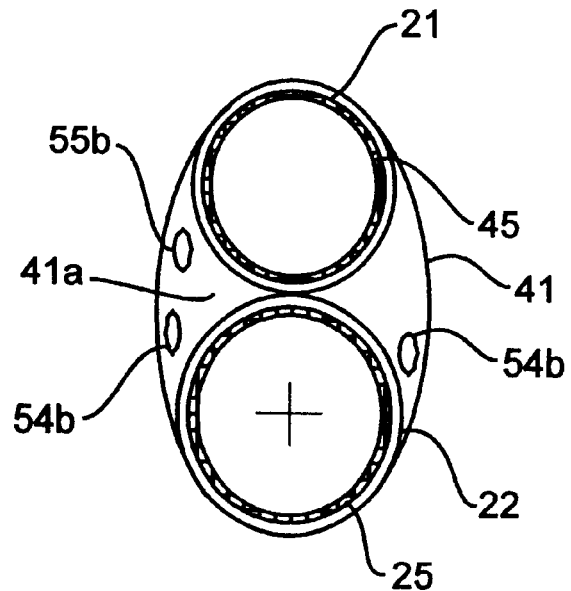
FIG. 4 is a cross-sectional view of the multi-lumen fluted balloon radiation centering catheter assembly of FIG. 1 taken along line C—C.

With reference to FIG. 4, for the four-lumen balloon embodiment shown in FIG. 3, three separate inflation lumens (54b, 55b) positioned proximal to the balloon 10 in a catheter shaft 41 are used to inflate the three balloon outer lumens 11. The inflation lumens (54b, 55b) communicate directly with each of the balloon outer lumens 11. A common inflation lumen 36, positioned within the catheter shaft outer member 46 (shown in FIG. 5), provides a common communication path between the inflation lumens (54b, 55b) (and thus the balloon outer lumens 11) and an inflation port 33 (shown in FIG. 1) to which a balloon inflation means (not shown) is attached. In this configuration, an inflation medium 18b enters the balloon catheter assembly at the inflation port 33, passes through the common inflation lumen 36 onto the three balloon inflation lumens (54b, 55b), and then enters and inflates the outer lumens 11 which causes the radiation source lumen 22 (and/or radiation source 25) to be centered within the :body vessel 16. The outer lumens 11 may be inflated at an operating pressure in the range of approximately 0.5–14 atmospheres. In one embodiment, the outer lumens 11 may be inflated at an operating pressure in the range of approximately 2–5 atmospheres.

For the multi-lumen balloon shown in FIG. 3, the central lumen 12 does not have to be pressurized and may not have to be sealed in order to inflate the balloon outer lumens 11. It should be noted that having individual inflation lumens for each of the balloon outer lumens allows each balloon outer lumen to be inflated to different pressures. This multi-lumen balloon arrangement is desirable for vessel treatment applications where the particular body vessel (in the area being treated) may not be fully circular (i.e., body vessel area may contain certain obstructions or "deposits" along its walls).

It should also be noted that it is not necessary to have individual inflation lumens (54b, 55b) for each of the balloon outer lumens 11 in order to center to radiation source lumen 22 with the vessel 16. For balloon designs where individual inflation lumens (54b, 55b) are absent, a catheter shaft inner lumen 41a may serve as a common inflation lumen for the balloon outer lumens 11.

Continuing with reference to FIG. 3, the diameter 18a of the balloon central lumen 12 is sized based on the radiation source outer diameter, for example a radiation source wire having an outer diameter in a range of approximately $10/1000$ in. to $50/1000$ in. The combined balloon diameter 13 (as measured across all balloon outer lumens 11 while balloon is in an inflated or deployed state) is kept in a range of approximately 1.5 mm to 6 mm for coronary vessels and in a range of approximately 3 mm to 12 mm for peripheral vessels. For the embodiment shown in FIG. 3, a balloon having a combined diameter 13 in a range of approximately 1.5 mm to 4 mm is advantageous when treating coronary vessels.

Referring to FIG. 11, another embodiment of the multi-lumen balloon of this invention is a balloon 10 having a central lumen 12 and a plurality of outer lumens 11 disposed around the central lumen 12. The outer lumens 11 are integrally coupled with the central lumen 12 so as to form the multi-lumen balloon 10. Bores (or channels) 35 are formed between;the outer lumens 11 and the central lumen 12. This arrangement allows an inflation medium 18b to pass from the balloon central lumen 12 into the outer lumens 11 and inflate outer lumens 11, causing a radiation source lumen 22 to be centered within a body vessel 16. In this configuration, the central lumen 12 may have to be pressurized in order for the outer lumens 11 to properly inflate and center the radiation source lumen 22 within the body vessel 16.

For the balloon configuration shown in FIG. 11, the balloon central lumen 12 is capable of containing a radiation source 25 (with or without a radiation source lumen 22) therein. The multi-lumen balloon embodiment shown in FIG. 11 is adapted for receiving a guidewire lumen (with a guidewire) through either one of its balloon outer lumens 11 or through its central lumen 12. Because in FIG. 11 the balloon 10 is shown as being used with a tip (or distal) Rapid Exchange catheter type (i.e., the guidewire is positioned distal to the balloon), for the balloon embodiment of FIG. 11, the guidewire does not extend through any of the balloon lumens 11.

Figure 6:
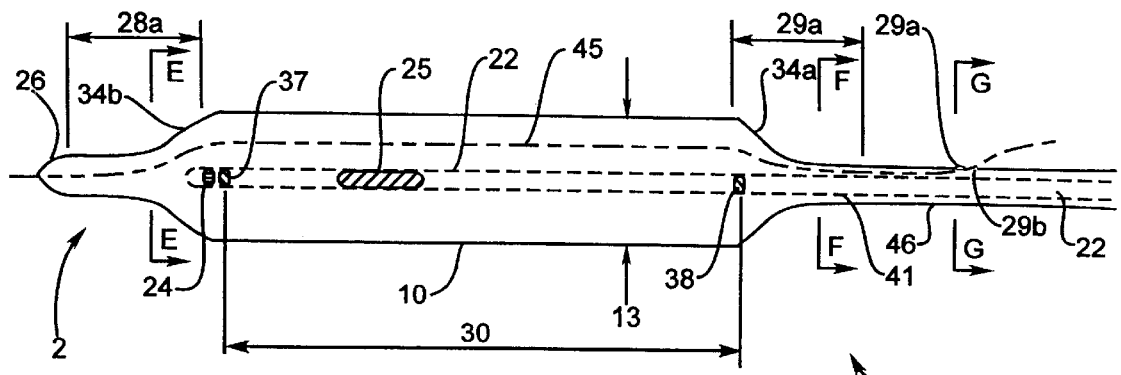
FIG. 6 is a side view of a second embodiment of a multi-lumen fluted balloon catheter assembly (standard-RX configuration) for centering radiation source, with proximal and distal slideable seals and without a guidewire lumen.
Figure 17:
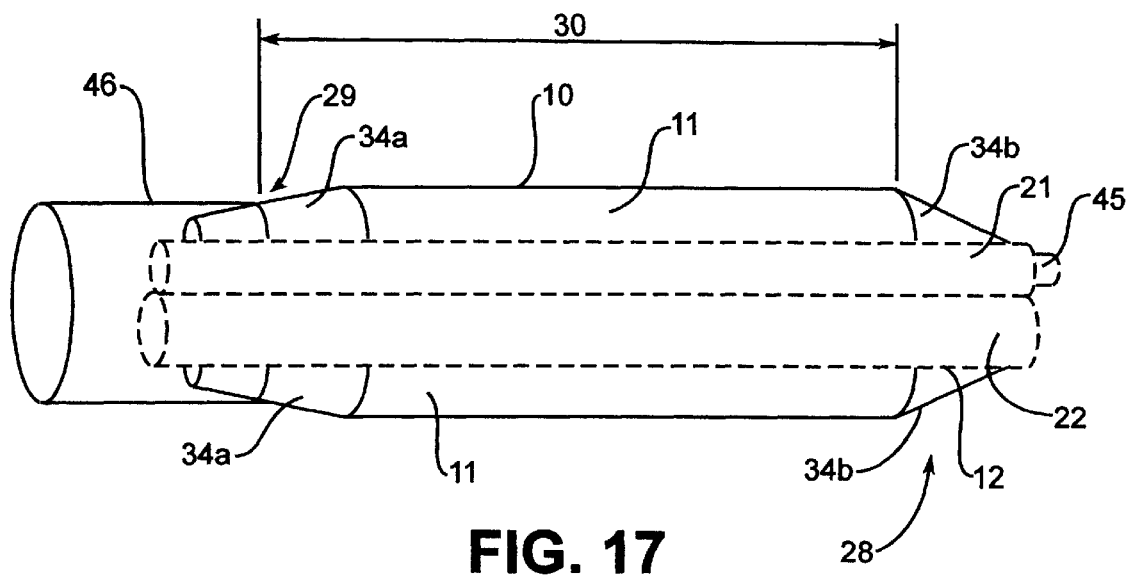
FIG. 17 is a schematic side view of the proximal and distal balloon seal areas for the fluted balloon radiation centering catheter assembly of FIG. 1.

It should be noted that while the balloon configuration of FIG. 3 shows a guidewire lumen 21 (with guidewire 45) extending through one of the balloon outer lumens 11, the guidewire 45 (with or without its guidewire lumen 21) may also be positioned so that it extends through the central lumen 12 of the multi-lumen balloon 10 (as shown in the balloon configuration of FIG. 14). Furthermore, whether a guidewire (and a guidewire lumen) extends through the multi-lumen balloon depends on a number of considerations, such as the type of catheter used, the balloon catheter manufacturing preferences, the treatment site configuration, etc. For example, when considering the type of catheter to be used, for a standard Rapid Exchange or an OTW catheter type, the guidewire 45 (with or without a guidewire lumen 21) would extend through one of the outer lumens (as shown in FIGS. 3, 6, and 17) or through the central lumen (as shown in FIG. 14). For balloon catheter assemblies using a tip (or distal) Rapid Exchange catheter type, because the guidewire (with or without a guidewire lumen) is positioned distal to the balloon, the guidewire would not extend through any of the balloon lumens (as shown in FIG. 11).

As with the other two balloon arrangements discussed above, for the balloon embodiment shown in FIG. 11 (i.e., having a "tip" or distal guidewire lumen that does not extend through the entire balloon lumen), the diameter 18a of the balloon central lumen 12 is sized based on the radiation source outer diameter, for example a radiation source wire having an outer diameter in a range of approximately $10/1000$ in. to $50/1000$ in. For the balloon embodiment shown in FIG. 14 (i.e., where the guidewire lumen 21 is positioned so that it extends through the central lumen 12), the diameter 18a of the balloon central lumen 12 is sized based on the radiation source outer diameter and the diameter of the guidewire lumen 21. Thus, the diameter 18a may be in a range of approximately $10/1000$ in. to $75/1000$ in. In one embodiment, the diameter 18a is $62/1000$ in.

Continuing with reference to FIG. 11, the combined balloon diameter 13 (as measured across all balloon outer lumens 11 while balloon is in an inflated or deployed state) is kept in a range of approximately 1.5 mm to 6 mm for coronary vessels and in a range of approximately 3 mm to 12 mm for peripheral vessels. For the embodiment shown in FIG. 11, a balloon having a combined diameter 13 in a range of approximately 1.5 mm to 4 mm is desirable when treating coronary vessels.

Referring now to FIG. 17, a four-lumen balloon 10 having a guidewire lumen 21 extending through one of the balloon outer lumens 11 is shown. Note that one of the outer lumens is hidden from view. A radiation source lumen 22 (capable of holding a radiation source) extends lengthwise through the balloon central lumen 12. The outer lumen 11 with the guidewire lumen 21 extending through it is also inflated as part of the function of the centering balloon catheter.

Continuing with reference to FIG. 17, the multi-lumen balloon 10 has a distal seal 28 and a proximal seal 29. Distal seal 28 seals the plurality of distal ends 34b of the balloon outer lumens 11 to a catheter shaft (formed by the radiation source lumen 22 and guidewire lumen 21) while the proximal seal 29 seals the plurality of proximal ends 34a of the balloon outer lumens 11 to the catheter shaft. The distal and proximal seals (28, 29) may each have a width in a range of approximately 0.5 mm to about 5 mm.

When balloon outer lumens' distal and proximal ends (34b, 34a) are sealed together into the distal seal and proximal seal respectively (28, 29), each of the outer lumens 11 takes the form of a "flute" (i.e., an elongated cylinder having tapered ends) when inflated by an inflation medium. The fluted balloon configuration shown in FIG. 17 is representative of balloon configurations of this invention (as shown in balloon catheter assemblies of FIGS. 1, 6, 10, and 13).

Referring to FIG. 1, a treatment area 30 is defined between the balloon's distal seal 28 and proximal seal 29. The longitudinal length of the balloon treatment area 30 is made to be appropriate for the body vessel to be treated (for example, coronary vessels or peripheral vessels) and for the radiation treatment to be delivered. In one embodiment of the present invention, the balloon treatment area length 30 is in a range of approximately 18 mm to 54 mm. For some intervascular gamma radiation treatments, such as treatments on peripheral vessels of the cardiovascular system, the balloon treatment area length 30 may be in a range of approximately 10 mm to 250 mm.

Referring now to FIG. 3, during vascular radiotherapy, when inflated and engaged with the walls of the body vessel 16, the balloon outer lumens 11 define a series of straight longitudinal paths 14 that allow for perfusion of blood (not shown) past balloon treatment area 30 (shown in FIG. 1).

The fluted balloon outer lumens 11 can be extruded with either equal diameter 15 (as shown in FIGS. 3, 11 and 18) or with unequal (or asymmetrical) diameter 15 (as shown in FIG. 14). A balloon 10 having outer lumens 11 with equal diameter 15 is well suited for a "standard Rapid Exchange" catheter (shown in FIGS. 3 and 6) or an "over-the-wire" catheter type, each having a guidewire lumen 21 (and/or a guidewire 45) extending through one of the balloon's outer lumens. A balloon 10 having outer lumens 11 with equal diameter 15 is also well suited for a "tip Rapid Exchange" catheter type having only the source wire lumen extending through a treatment channel 50 contained within the balloon central lumen 12 (shown in FIG. 11).

Referring to FIG. 14, fluted outer lumens 11 with unequal diameter 15 would provide the offset necessary to compensate for the slight eccentricity in the location of a treatment channel 50 (with the radiation source wire lumen 22 in it) within the central lumen 12 of the balloon 10. A balloon arrangement having outer lumens 11 with unequal diameters (for example, a balloon assembly with one small "flute" and two large "flutes") is best suited for the "standard RX" or "over-the-wire" catheter designs where the catheter shaft (or inner member) 41 includes two parallel lumens: a source lumen 22 (for a radiation source 25) and a guidewire lumen 21 (for a guidewire 45). For very small diameter centering balloon catheters, such as the 2 mm diameter balloon catheter designs, the small "flute" 11 shown in FIG. 14 may be eliminated to provide for centering of the radiation source lumen 22.

The multi-lumen balloon 10 is manufactured using balloon materials, such as Pebax™, nylon, polyethylene, polyurethane, or polyester. Materials for use in fabricating the multi-lumen balloon 1 0 of the present invention are selected by considering the properties and characteristics (e.g., softness, durability, low stiffness) required by angioplasty balloons, as well as considering properties necessary for successful balloon fabrication (e.g., balloon material compatible with other catheter materials and bonding process, material extruding well, etc.). When deployed (i.e., inflated), the multi-lumen balloon 10 is a high strength, flexible, reasonably noncompliant balloon. The fluted shape of the balloon outer lumens allows the balloon to have improved blood perfusion capability as well as improved balloon refolding characteristics (where the inflation medium is removed from the balloon outer lumens).

Fluted Balloon Radiation Centering Catheter Assembly

Figure 12:
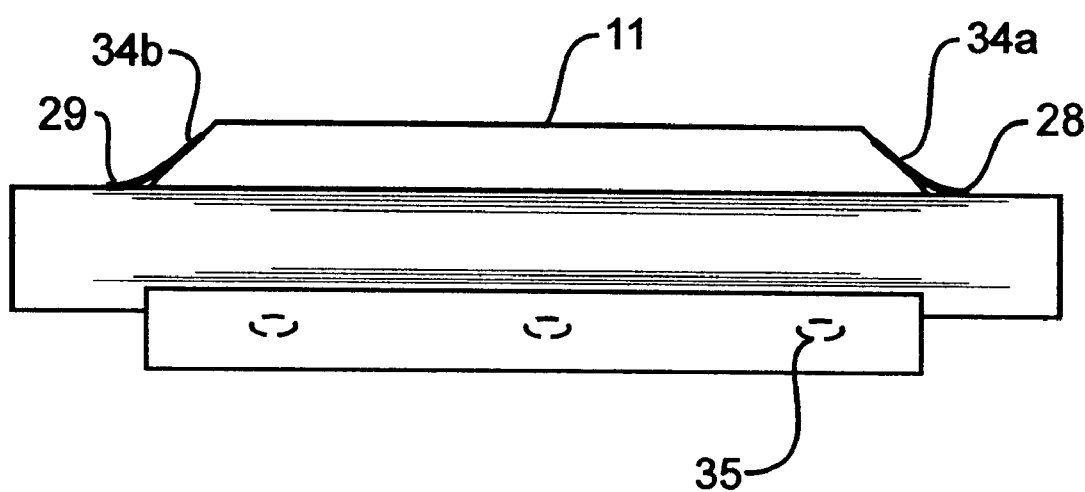
FIG. 12 is a partial longitudinal cross-sectional view of the multi-lumen fluted balloon catheter assembly of FIG. 10 taken along line J—J showing a configuration for inflation/deflation and attachment.

With reference to FIGS. 1–16, four types of fluted balloon radiation centering catheter assemblies are illustrated. In FIGS. 1–5, a fluted balloon radiation centering catheter assembly 1 for a "standard Rapid Exchange" catheter with a guidewire lumen 21 extending through one of the outer lumens is shown. In FIGS. 5–9, a fluted balloon radiation centering catheter assembly 1 for a standard Rapid Exchange catheter 2 with proximal and distal slideable seals is shown. In FIGS. 10–12, a fluted balloon radiation centering catheter assembly 1 for a "tip (or distal) Rapid Exchange" catheter 2 is illustrated. Finally, in FIGS. 13–16, a fluted balloon radiation centering catheter assembly 1 for a standard Rapid Exchange catheter 2 with a guidewire lumen 21 extending through the central lumen 12 is shown.

Multi-lumen Balloon Catheter Having a Guidewire Lumen Through Balloon Outer Lumen Referring to FIG. 1, a multi-lumen fluted balloon radiation centering catheter assembly 1 with the balloon 10 in an inflated state is shown. The fluted balloon radiation centering catheter assembly 1 includes a multi-lumen balloon 10 and an interventional catheter 2. Interventional catheter 2 has a shaft 41 disposed proximate the balloon 10. The balloon 10 includes a plurality of inflatable outer lumens 11 disposed around a central lumen 12, the plurality of outer lumens 11 integrally coupled with the central lumen 12 so as to form the multi-lumen balloon 10. The balloon 10 has a distal seal 28 and a proximal seal 29. Distal seal 28 seals the plurality of distal ends 34b of the balloon outer lumens 11 to the catheter shaft 41 while the proximal seal 29 seals the, plurality of proximal ends 34a of the balloon outer lumens 11 to the catheter shaft 41. Each of the outer lumens 11 takes the form of a "flute" (i.e., an elongated cylinder having tapered ends) when inflated by an inflation medium 18b (shown in FIG. 3 for this balloon catheter assembly). A fluted balloon configuration is shown in FIG. 17, which is a representative illustration of balloon configurations of this invention (as revealed in balloon catheter assemblies of FIGS. 1, 6, 10, and 13).

Referring now to FIG. 3, the multi-lumen balloon catheter assembly 1 has a radiation source lumen 22 that extends longitudinally through the central lumen 12 of the four-lumen balloon 10. In one embodiment, for a "standard Rapid Exchange" (standard RX) or an "over-the-wire" (OTW) catheter type, a guidewire lumen 21 (capable of containing a guidewire 45) extends through one of the balloon outer lumens (as shown in FIG. 3). The guidewire 45 allows positioning the multi-lumen centering catheter 1 (including its radiation source lumen 22) on the stenosed body vessel area 16 for patient treatment.

The balloon radiation centering catheter assembly shown in FIG. 3 may also be used with a "tip (or distal) Rapid Exchange" catheter type, with a guidewire lumen 21 is distally positioned to the multi-lumen balloon 10 and thus would not pass through the balloon 10.

For a "Standard RX" catheter type, the guidewire exists the catheter shaft at a distance in a range of approximately 15–35 cm from the distal tip of the catheter. For a "tip RX" catheter type, the guidewire exists the catheter shaft at a distance in a range of approximately 3–20 mm from the distal tip of the catheter. Note that for a tip RX catheter type, the guidewire does not enter the balloon. For the "OTW" catheter type, the guidewire extends through the catheter shaft. The distance from the distal tip of the catheter to the inflation port may be in a range of approximately 75–135 cm for coronary applications and in a range of approximately 75–145 cm for peripheral applications. For any catheter type, if an afterloader (i.e., radiation therapy device) is to be used, the guidewire may be extended an additional 15–125 cm. In one embodiment, when using the afterloader the guidewire extension may be in a range of approximately 70–80 cm.

Continuing with reference to FIG. 3, as mentioned above, the radiation source lumen 22 extends longitudinally through the balloon central lumen and the standard RX guidewire lumen 21 extends longitudinally through one of the balloon outer lumens 11. The remaining two outer lumens 11 are then sealed onto the radiation source lumen 22 and the guidewire lumen 21 for maintaining inflation pressure in the balloon. When inflated by an inflation medium 18b, the balloon outer lumens 11 form flutes positioned parallel to the radiation source lumen 22 and the guidewire lumen 21. During vascular radiotherapy, when inflated and engaged with the walls of the body vessel 16, the balloon outer lumens 11 define a series of straight longitudinal paths 14 that allow for perfusion of blood (not shown) past balloon treatment area 30 (shown in FIG. 1).

The fluted balloon outer lumens 11 can be extruded with either equal diameter 15 (as shown in FIGS. 3, 11 and 18) or with unequal (or asymmetrical) diameter 15 (as shown in FIG. 14). A balloon 10 having outer lumens 11 with equal diameter 15 is well suited for a "standard Rapid Exchange" catheter (shown in FIGS. 3 and 6) or an "over-the-wire" catheter type, each having a guidewire lumen 21 (and/or a guidewire 45) extending through one of the balloon's outer lumens. A balloon 10 having outer lumens 11 with equal diameter 15 is also well suited for a "tip Rapid Exchange" catheter type having only the source wire lumen extending through a treatment channel 50 contained within the balloon central lumen 12 (shown in FIG. 11).

Continuing with reference to FIG. 3, the diameter 18a of the balloon central lumen 12 is sized based on the radiation source outer diameter, for example a radiation source wire having an outer diameter in a range of approximately $10/1000$ in. to $50/1000$ in. The combined balloon diameter 13 (as measured across all balloon outer lumens 11 while balloon, is in an inflated or deployed state) is kept in a range of approximately 1.5 mm to 6 mm for coronary vessels and in a range of approximately 3 mm to 12 mm for peripheral vessels. For the embodiment shown in FIG. 3, a balloon having a combined diameter 13 in a range of approximately 1.5 mm to 4 mm is advantageous when treating coronary vessels.

Referring to FIG. 4 (which represents a cross-sectional view of the multi-lumen fluted balloon radiation centering catheter assembly of FIG. 1 taken along line C—C), the catheter shaft 41 includes an inner lumen 41a that extends longitudinally through at least a portion of the catheter shaft 41 proximate the balloon 10 and connects to the central lumen 12 of the balloon 10. The catheter shaft inner lumen 41a is adapted for receiving a radiation source lumen 22 with a radiation source 25 and a guidewire lumen 21 capable of containing a guidewire 45 for positioning the multi-lumen balloon radiation centering catheter 1 within a body vessel. Both the radiation source lumen 22 and the guidewire lumen 21 are manufactured as co-extrusions having an inner layer made of a material such as polyethylene and an outer layer made of a material such as Pebax, nylon, or Primacor.

Continuing with reference to FIG. 4, the catheter shaft inner lumen 41a is further adapted to receive at least one inflation lumen (54b, 55b) that is in fluid communication with each of the balloon outer lumens to allow an inflation fluid to enter and inflate the outer lumens 11 and thus, center the radiation source lumen 22 within a body vessel 16. The inflation lumen(s) (54b, 55b) in the catheter shaft inner lumen 41a are generally formed when the multi-lumen balloon 10 is bonded to the catheter shaft 41 during the catheter proximal seal 29 construction (explained in more detail in the Proximal Seal section).

As mentioned above, having individual inflation lumens for each of the balloon outer lumens allows each balloon outer lumen to be inflated to different pressures. However, it is not necessary to have individual inflation lumens for each of the balloon outer lumens in order to center to radiation source lumen with the vessel. For balloon catheter designs where individual inflation lumens (54b, 55b) are absent, the catheter shaft inner lumen 41a may serve as an inflation lumen for the balloon outer lumens 11.

Figure 5:
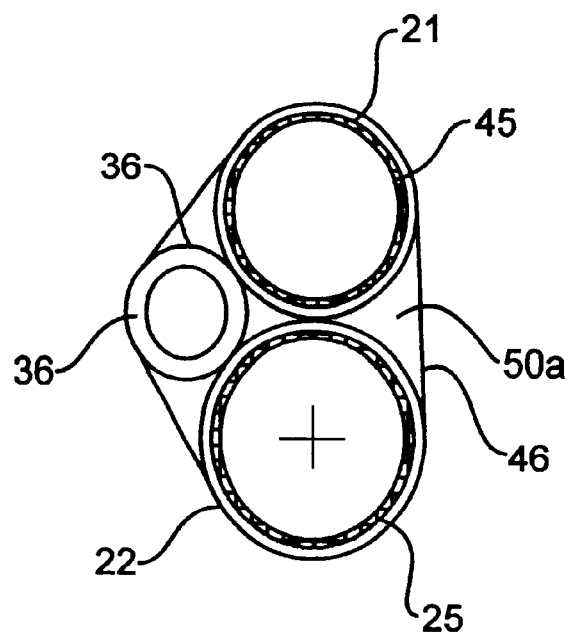
FIG. 5 is a cross-sectional view of the multi-lumen fluted balloon radiation centering catheter assembly of FIG. 1 taken along line D—D.

Referring to FIG. 5 (which represents a cross-sectional view of the multi-lumen fluted balloon radiation centering catheter assembly of FIG. 1 taken along line D—D), at the region of the balloon catheter proximal seal 29, an elongated flexible catheter outer member 46 is placed over the catheter shaft 41. The catheter outer member may be manufactured of materials such as nylon, Pebax, polyurethane, etc. Catheter outer member 46 includes a lumen 50a that extends longitudinally therein. Near the catheter proximal seal 29 region, the lumen 50a becomes the catheter shaft inner lumen 41a. Lumen 50a is adapted for receiving a common inflation lumen 36 for inflating and pressurizing the balloon outer lumens 11 with an inflation medium (or means) 18b. The inflation medium 18b could include any inflation medium known in the art of balloon angioplasty, such as air, saline solution, or contrast fluid.

Continuing with reference to FIG. 5, the catheter outer member inner lumen 50a is adapted for receiving a radiation source lumen 22 with a radiation source 25. If a Standard RX (Rapid Exchange) or an OTW interventional catheter assembly 2 is used, the catheter outer member lumen 50a is further adapted for receiving a guidewire lumen 21 (and/or a guidewire 45).

Referring now to FIG. 1, the multi-lumen balloon has a treatment area 30 is defined between the balloon's distal seal 28 and proximal seal 29. The longitudinal length of the balloon treatment area 30 is made to be appropriate for the body vessel to be treated (for example, coronary vessels or peripheral vessels) and for the radiation treatment to be delivered. In one embodiment of the present invention, the balloon treatment area length 30 is in a range of approximately 18 mm to 54 mm. For some intervascular gamma radiation treatments, such as treatments on peripheral vessels of the cardiovascular system, the balloon treatment area length 30 may be in a range of approximately 10 mm to 250 mm.

Continuing with reference to FIG. 1, in one embodiment, the radiation source lumen 22 is sealed at its distal end 23 with plug 24 to allow a radiation source 25 to be placed inside the radiation source lumen 22. In another embodiment, the radiation source lumen 22 is left open at its distal end 23 (i.e., it does not have a plug 24) so that a radiation source 25 (placed inside the radiation source lumen 22) can be distally advanced past the multi-lumen balloon 10. Furthermore, not having the radiation source lumen 22 sealed with the plug 24 decreases the stiffness of the multi-lumen balloon even further.

It should be noted that it is not necessary to have a radiation source lumen 22 as part of the multi-lumen balloon centering catheter assembly 1. In some applications, it may be desirable to place the radiation source 25 directly within the central lumen 12 of the balloon 10, without employing a source lumen 22. Not having a radiation source lumen 22 in the balloon central lumen 12 reduces the size of the multi-lumen balloon and decreases the stiffness of the multi-lumen balloon (since the radiation source lumen 22 is a co-extruded shaft), thus allowing the balloon to cross tortuous paths more easily along the body vessel.

The radiation source 25, which may be shaped in the form of a wire, seed, pellets, ribbon, etc., is positioned inside radiation source lumen 22 and is then advanced longitudinally along a prescribed vessel length 16 during patient treatment. In one embodiment of this invention, the multi-lumen balloon centering catheter assembly 1 uses a Phosphorus-32 radiation source as a radiation source 24. However, the multi-lumen balloon of this invention can be used with any radiation source employed in vascular radiotherapy, which includes gamma radiation emitting sources and beta radiation emitting sources known in the art.

Continuing with reference to FIG. 1, two radio-opaque markers, a distal marker 37 and a proximal marker 38, may be attached to the radiation source lumen 22. The radio-opaque markers 37 and 38 are used for positioning the interventional catheter 1 under fluoroscopy, as well as for assisting the stepping (via manual or automatic means) of the radiation source 25 over the entire prescribed region of the vessel 16 to be treated. The markers 37 and 38 are made of any materials known in the art of radio-opaque markers, such as silver, gold, platinum, tungsten, that allow markers to become visible under fluoroscopy. In one embodiment, the radio-opaque markers (37, 38) are attached within the limits of the balloon's treatment area 30. In one configuration, the distal marker 37 is incorporated into the plug 24 of the source lumen 22. In another configuration, radio-opaque markers (37, 38) may be part of a separate device (not shown) that is independent of the balloon catheter assembly.

A soft tip 26 is attached to the distal end 27 of the guidewire lumen 21 to improve trackability and reduce trauma to the body vessel. The length of the soft tip 26 depends on the type of catheter design used, however, the length of the tip is generally in a range of approximately 0.5 mm to 10 mm.

With reference to FIG. 1, the balloon 10 is attached to catheter shaft 41 of the catheter assembly 2. The ballodn's proximal seal 29 is attached at a proximal end 44 of flexible catheter shaft 41, near the inflation/deflation port 33. The balloon distal seal 28 is attached to the catheter shaft 41 adjacent to the location where the radiation source lumen 22 ends. In one embodiment, the balloon 10 and assembly 2 are attached by using a laser bond technique. Bonds may also be done using other balloon bonding techniques known in the art, such as thermal or ultrasonic welds, adhesive welds, or other conventional means. The distal and proximal seals (28, 29) may each have a width in a range of approximately 0.5 mm to about 5 mm.

Multi-lumen Balloon Catheter Having a Slideable Proximal Seal and a Slideable Distal Seal Referring to FIGS. 6–9, a fluted balloon radiation centering catheter assembly for a standard Rapid Exchange catheter with proximal and distal slideable seals is shown. In the embodiment disclosed herein, the tubing used to form the guidewire lumen is eliminated, and is replaced by proximal slideable seal 29a and distal slideable seal 28a as shown in FIG. 6. Eliminating the guidewire tubing reduces the material used and lowers the balloon catheter proximal seal outer diameter. These improvements make the catheter less stiff, allowing the balloon catheter to cross tortuous paths more easily along the body vessel. Furthermore, eliminating the guidewire tubing allows the proximal seal to become less complicated during seal manufacturing (as discussed in more detail in a later section).

With reference to FIG. 6, the path of the rapid exchange guidewire 45 starts at the distal tip 26 of the catheter 1 by entering an annular space 45b (shown in FIG. 7) formed between the catheter shaft 41 and the distal end of the radiation source lumen 22. This is where the slideable distal seal 28a is located. The guidewire 45 then longitudinally passes through one of the balloon outer lumens 11, where the balloon outer lumen 11 itself acts as a guidewire lumen. The guidewire 45 then runs in the annular space 52 (shown in FIG. 8) between the shaft outer member 46 and the source lumen 22 until it reaches an exit notch 29b with a slideable proximal seal 29a. These annular spaces 45b and 52 are also used to inflate and deflate the multi-lumen balloon, so "slideable" seals are used at both the catheter tip 26 and at the guidewire exit notch 29b.

Figure 7:
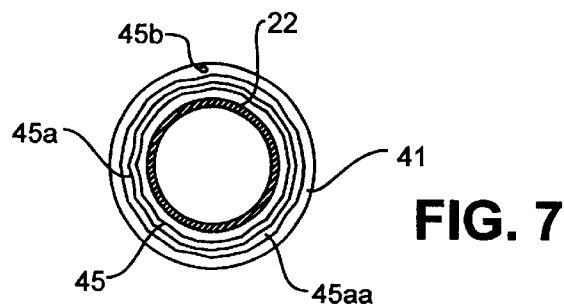
FIG. 7 is a cross-sectional view of the multi-lumen fluted balloon radiation centering catheter assembly of FIG. 6 taken along line E—E.

Referring to FIG. 7, as stated above, the guidewire 45 enters an annular space 45b (shown in FIG. 7) formed between the catheter shaft 41 and the distal end of the radiation source lumen 22. To create the slideable distal seal 28a, the annular space 45b is made to be a "close fit" by having a minimal distance clearance between the outer diameter of the guidewire 45 and the inner diameter of the balloon seal (formed when the balloon is being bonded to the catheter shaft).

Figure 8:
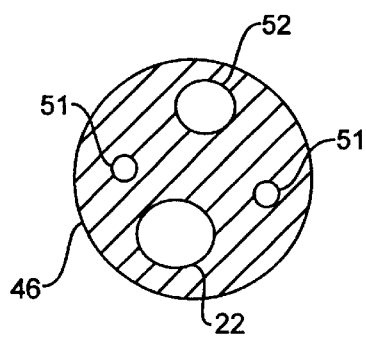
FIG. 8 is a cross-sectional view of the multi-lumen fluted balloon radiation centering catheter assembly of FIG. 6 taken along line F—F.

Referring to FIG. 8, after exiting the balloon outer lumen, the guidewire 45 then enters an annular space 52 (shown in FIG. 8) formed in the catheter shaft outer member 46. The annular space (or lumen) 52 serves both as a lumen for the guidewire 45 and as an inflation lumen for the balloon outer lumen that has the guidewire contained therein.

The slideable distal and proximal seals (28a, 29a) prevent the balloon inflation media (for example, saline) (not shown) from leaking out of the catheter 2. However, the slideable seals (28a, 29a) to the guidewire 45 are not fixed, rather the design allows the guidewire to slide axially relative to the catheter 2 and also allows the guidewire 45 to be rotated relative to the catheter. In one embodiment, the combination of a sealing capability with relative motion is obtained by having minimal clearances between the outer diameter of the guidewire 45 and the inner diameter 45aa of the seal formed between the balloon and the catheter shaft (as shown in FIG. 7).

Another embodiment of the slideable proximal and distal seals uses a hydrogel material 45a (shown in FIG. 7), positioned either on the guidewire 45 or integral to the slideable distal and proximal seals (28a, 29a) to maintain the pressure seal while providing smoother movement of the guidewire 45. To insure that the seals (28a, 29a) hold pressure, the catheter 2 may be used with guidewires that have a polymer jacket rather than an intermediate wire coil. In a yet another embodiment, the hydrogel material in the slideable proximal and distal seals is substituted with an O-ring 45a (shown in FIG. 9). This O-ring is positioned either on the guidewire 45 or integral to the slideable distal and proximal seals (28a, 29a) to maintain the pressure seal while providing smoother movement of the guidewire 45.

Referring to FIG. 6, a multi-lumen fluted balloon radiation centering catheter assembly 1 with the balloon 10 in an inflated state is shown. The fluted balloon radiation centering catheter assembly 1 includes a multi-lumen balloon 10 and an interventional catheter 2. Interventional catheter 2 has a shaft 41 disposed proximate to the balloon 10. The balloon 10 includes a plurality of inflatable outer lumens 11 disposed around a central lumen 12, the plurality of outer lumens 11 integrally coupled with the central lumen 12 so as to form the multi-lumen balloon 10. The balloon 10 has a slideable distal seal 28a and a slideable proximal seal 29a. Slideable distal seal 28a seals the plurality of distal ends 34b of the balloon outer lumens 11 to the catheter shaft 41 while the slideable proximal seal 29a seals the plurality of proximal ends 34a of the balloon outer lumens 11 to the catheter shaft 41.

Each of the outer lumens 11 takes the form of a "flute" (i.e., an elongated cylinder having tapered ends) when inflated by an inflation medium. A fluted balloon configuration is shown in FIG. 17, which is a representative illustration of balloon configurations of this invention. During vascular radiotherapy, when inflated and engaged with the walls of the body vessel 16, the balloon outer lumens 11 define a series of straight longitudinal paths that allow for perfusion of blood past a balloon treatment area 30 (shown in FIG. 6). The longitudinal length of the balloon treatment area 30 is made to be appropriate for the body vessel to be treated (for example, coronary vessels or peripheral vessels) and for the radiation treatment to be delivered. In one embodiment of the present invention, the balloon treatment area length 30 is in a range of approximately 18 mm to 54 mm. For some intervascular gamma radiation treatments, such as treatments on peripheral vessels of the cardiovascular system, the balloon treatment area length 30 may be in a range of approximately 10 mm to 250 mm.

The fluted balloon outer lumens 11 can be extruded with either equal diameter 15 (as shown in FIGS. 3, 11 and 18) or with unequal (or asymmetrical) diameter 15 (as shown in FIG. 14).

Continuing with reference to FIG. 6, the balloon central lumen 12 is sized based on the radiation source outer diameter, for example a radiation source wire having an outer diameter in a range of approximately $19/1000$ in. to $59/1000$ in. The combined balloon diameter 13 (as measured across all balloon outer lumens 11 while balloon is in an inflated or deployed state) is kept in a range of approximately 1.5 mm to 6 mm for coronary vessels and in a range of approximately 3 mm to 12 mm for peripheral vessels. For the embodiment shown in FIG. 6, a balloon having a combined diameter 13 in a range of approximately 1.5 mm to 4 mm is advantageous when treating coronary vessels.

Continuing with reference to FIG. 6, the multi-lumen balloon catheter assembly 1 has a radiation source lumen 22 that extends longitudinally through the central lumen 12 of the four-lumen balloon 10. In this embodiment, a guidewire 45 without a guidewire lumen tubing extends through one of the balloon outer lumens (as shown in FIG. 6). The guidewire 45 allows positioning the multi-lumen centering catheter 1 (including its radiation source lumen 22) on the stenosed body vessel area for patient treatment.

Continuing with reference to FIG. 6, in one embodiment, the radiation source lumen 22 is sealed at its distal end with plug 24 to allow a radiation source 25 to be placed inside the radiation source lumen 22. In another embodiment, the radiation source lumen 22 is left open at its distal end 23 (i.e., it does not have a plug 24) so that a radiation source 25 (placed inside the radiation source lumen 22) can be distally advanced past the multi-lumen balloon 10. Furthermore, not having the radiation source lumen 22 sealed with the plug 24 decreases the stiffness of the multi-lumen balloon even further.

It should be noted that it is not necessary to have a radiation source lumen 22 as part of the multi-lumen balloon centering catheter assembly 1. In some applications, it may be desirable to place the radiation source 25 directly within the central lumen 12 of the balloon 10, without employing a source lumen 22. Not having a radiation source lumen 22 in the balloon central lumen 12 reduces the size of the multi-lumen balloon and decreases the stiffness of the multi-lumen balloon (since the radiation source lumen,22 is a co-extruded shaft), thus allowing the balloon to cross tortuous paths more easily along the body vessel.

The radiation source 25, which may be shaped in the form of a wire, seed, pellets, ribbon, etc., is positioned inside radiation source lumen 22 and is then advanced longitudinally along a prescribed vessel length 16 during patient treatment. In one embodiment of this invention, the multi-lumen balloon centering catheter assembly 1 uses a Phosphorus-32 radiation source as a radiation source 24. However, the multi-lumen balloon of this invention can be used with any radiation source employed in vascular radiotherapy, which includes gamma radiation emitting sources and beta radiation emitting sources known in the art.

Continuing with reference to FIG. 6, two radio-opaque markers, a distal marker 37 and a proximal marker 38, may be attached to the radiation source lumen 22. The radio-opaque markers 37 and 38 are used for positioning the interventional catheter 1 under fluoroscopy, as well as for assisting the stepping (via manual or automatic means) of the radiation source 25 over the entire prescribed region of the vessel 16 to be treated. The markers 37 and 38 are made of any materials known in the art of radio-opaque markers, such as silver, gold, platinum, tungsten, that allow markers to become visible under fluoroscopy. In one embodiment, the radio-opaque markers (37, 38) are attached within the limits of the balloon's treatment area 30. In one configuration, the distal marker 37 is incorporated into the plug 24 of the source lumen 22. In another configuration, radio-opaque markers (37, 38) may be part of a separate device (not shown) that is independent of the balloon catheter assembly.

A soft tip 26 (shown in FIG. 6) is attached to the distal end 27 of the guidewire 45 to improve trackability and reduce trauma to the body vessel. The length of the soft tip 26 depends on the type of catheter design used, however, the length of the tip is generally in a range of approximately 0.5 mm to 10 mm.

Referring now to FIG. 8 (which represents a cross-sectional view of the multi-lumen fluted balloon radiation centering catheter assembly of FIG. 6 taken along line F—F), the catheter shaft 41 includes an inner lumen 41a that extends longitudinally through at least a portion of the catheter shaft 41 proximate the balloon 10 and connects to the central lumen 12 of the balloon 10. The catheter shaft inner lumen 41a is adapted for receiving a radiation source lumen 22 with a radiation source 25. The radiation source lumen 22 is manufactured as a co-extruded shaft having an inner layer made of a material such as polyethylene and an outer layer made of a material such as Pebax, nylon, or Primacor.

Continuing with reference to FIG. 8, the catheter shaft inner lumen 41a is further adapted to receive a plurality of inflation lumens (51, 52) that are in fluid communication with each of the balloon outer lumens to allow an inflation fluid to enter and inflate the outer lumens 11 and thus, center the radiation source lumen 22 within a body vessel 16. Note that lumen 52 serves as both an inflation lumen and as a guidewire lumen. The inflation lumens (51, 52) in the catheter shaft inner lumen 41a are generally formed when the multi-lumen balloon 10 is bonded to the catheter shaft 41 during the catheter slideable proximal seal 29a construction. As mentioned above, having individual inflation lumens for each of the balloon outer lumens allows each balloon outer lumen to be inflated to different pressures.

Figure 9:
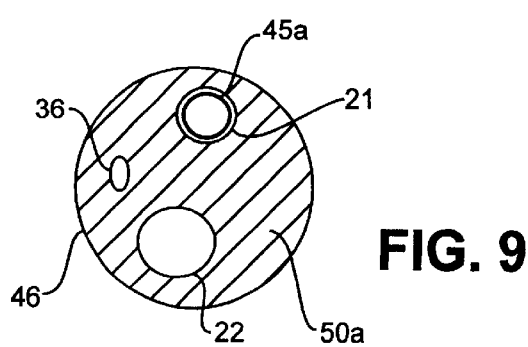
FIG. 9 is a cross-sectional view of the multi-lumen fluted balloon radiation centering catheter assembly of FIG. 6 taken along line G—G.
Figure 10:
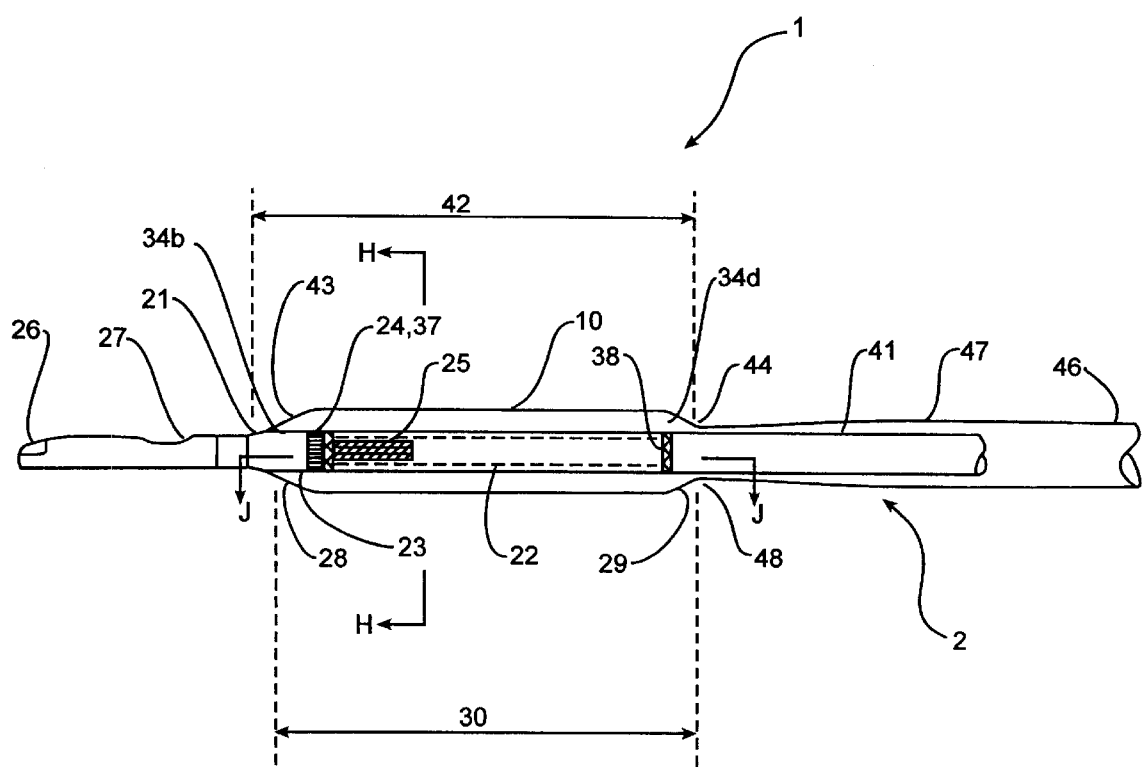
FIG. 10 is a side view of a third embodiment of the multi-lumen fluted balloon catheter assembly (for a tip-RX configuration) for centering a radiation source.

Referring to FIG. 9 (which represents a cross-sectional view of the multi-lumen fluted balloon radiation centering catheter assembly of FIG. 6 taken along line G—G), at the region of the balloon catheter slideable proximal seal 29a, an elongated flexible catheter outer member 46 is placed over the catheter shaft 41. Catheter outer member 46 includes a lumen 50a that extends longitudinally therein. Past the catheter slideable proximal seal 29a region, the lumen 50a becomes the catheter shaft inner lumen 41a.

Lumen 50a is adapted for receiving a common inflation lumen 36 for inflating and pressurizing the balloon outer lumens 11 with an inflation medium (or means) 18b. The inflation medium 18b could include any inflation medium known in the art of balloon angioplasty, such as air, saline solution, or contrast fluid. The catheter outer member inner lumen 50a is further adapted for receiving a radiation source lumen 22 (with a radiation source) and a guidewire lumen 21. At the slideable proximal seal 29a, to ensure a tight and close fit, the guidewire lumen 21 in the catheter outer member 46 is adapted for receiving a hydrogel material or an O-ring 45a. The catheter outer member 46 may be manufactured of materials such as nylon, Pebax, polyurethane, etc.

Multi-lumen Balloon Catheter Having a Balloon with Communication Bores between Central and Outer Lumens and a Tip Rapid Exchange Guidewire Lumen With reference to FIGS. 10–16, two embodiments of a multi-lumen fluted balloon radiation centering catheter assembly are shown. Both catheter assemblies include a multi-lumen balloon having communication bores between the central lumen and the outer lumens. In FIGS. 10–12, a fluted balloon radiation centering catheter assembly for a "tip (or distal) Rapid Exchange" catheter 2 is illustrated, while in FIGS. 13–16, a fluted balloon radiation centering catheter assembly 1 for a standard Rapid Exchange catheter with a guidewire lumen extending through the central lumen is shown.

Referring to FIG. 10, a multi-lumen fluted balloon radiation centering catheter assembly 1 with the balloon 10 in an inflated state is shown. The fluted balloon radiation centering catheter assembly 1 includes a multi-lumen balloon 10 and an interventional catheter 2. Interventional catheter 2 has a shaft disposed proximate the balloon 10. The balloon 10 includes a plurality of inflatable outer lumens 11 disposed around a central lumen 12, the plurality of outer lumens 11 integrally coupled with the central lumen 12 so as to form the multi-lumen balloon 10. The balloon 10 has a distal seal 28 and a proximal seal 29. Distal seal 28 seals the plurality of distal ends 34b of the balloon outer lumens 11 to the catheter shaft 41 while the proximal seal 29 seals the plurality of proximal ends 34a of the balloon outer lumens 11 to the catheter shaft 41. The distal and proximal seals (28, 29) may each have a width in a range of approximately 0.5 mm to about 5 mm.

Each of the outer lumens 11 takes the form of a "flute" (i.e., an elongated cylinder having tapered ends) when inflated by an inflation medium 18b (shown in FIG. 11 for this balloon catheter assembly). A fluted balloon configuration is shown in FIG. 17, which is a representative illustration of balloon configurations of this invention (as revealed in balloon catheter assemblies of FIGS. 1, 6, 10, and 13).

Continuing with reference to: FIG. 10, the catheter shaft includes an inner tubular member 41 having a distal treatment section 42 with a distal end 43 and a proximal end 44, and a proximate section (not shown). The inner tubular member 41 has an inner lumen 41a. The catheter shaft further includes a flexible elongate outer tubular member 46 having a distal section 47 with a distal end 48, and a proximate section (not shown). Elongate inner tubular member 41 extends coaxially within the elongate outer tubular member 46.

Referring now to FIG. 11, the balloon central lumen 12 is capable of containing a radiation source 25 (with or without a radiation source lumen 22) therein. The multi-lumen balloon embodiment shown in FIG. 11 is adapted for receiving a guidewire lumen (with a guidewire) through its central lumen 12 (as shown in FIG. 14). Because in FIG. 11 the balloon 10 is shown as being used with a tip (or distal) Rapid Exchange catheter type (i.e., the guidewire is positioned distal to the balloon), for the balloon embodiment of FIG. 11, the guidewire does not extend through any of the balloon lumens 11.

For the balloon configuration shown in FIG. 11, the balloon 10 includes bores (or channels) 35 that are formed between the outer lumens 11 and the central lumen 12. This arrangement allows an inflation medium 18b to pass from the balloon central lumen 12 into the outer lumens 11 and inflate outer lumens 11, causing a radiation source lumen 22 to be centered within a body vessel 16. In this configuration, the central lumen 12 is pressurized in order for the outer lumens 11 to properly inflate and center the radiation source lumen 22 within the body vessel 16. The catheter inner lumen 41a is adapted to serve as an inflation lumen for the balloon central lumen 12 and the outer lumens 11.

Continuing with reference to FIG. 11, as mentioned above, the radiation source lumen 22 extends longitudinally through the balloon central lumen. When using a tip RX radiation catheter type, the plurality of outer lumens 11 are sealed onto the radiation source lumen 22 for maintaining inflation pressure in the balloon. When inflated by an inflation medium 18b, the balloon outer lumens 11 form flutes positioned parallel to the radiation source lumen 22. During vascular radiotherapy, when inflated and engaged with the walls of the body vessel 16, the balloon outer lumens 11 define a series of straight longitudinal paths 14 that allow for perfusion of blood (not shown) past balloon treatment area 30 (shown in FIG. 10).

The fluted balloon outer lumens 11 can be extruded with either equal diameter 15 (as shown in FIG. 11) or with unequal (or asymmetrical) diameter 15 (as shown in FIG. 14). A balloon 10 having outer lumens 11 with equal diameter 15 is well suited for a "tip Rapid Exchange" catheter type having only the source wire lumen extending through a treatment channel 50 contained within the balloon central lumen 12 (shown in FIG. 11).

Continuing with reference to FIG. 11, the diameter 18a of the balloon central lumen 12 is sized based on the radiation source outer diameter, for example a radiation source wire having an outer diameter in a range of approximately $10/1000$ in. to $50/1000$ in. The combined balloon diameter 13 (as measured across all balloon outer lumens 11 while balloon is in an inflated or deployed state) is kept in a range of approximately 1.5 mm to 6 mm for coronary vessels and in a range of approximately 3 mm to 12 mm for peripheral vessels. For the embodiment shown in FIG. 11, a balloon having a combined diameter 13 in a range of approximately 1.5 mm to 4 mm is advantageous when treating coronary vessels.

Referring now to FIG. 10, the multi-lumen balloon has a treatment area 30 is defined between the balloon's distal seal 28 and proximal seal 29. The longitudinal length of the balloon treatment area 30 is made to be appropriate for the body vessel to be treated (for example, coronary vessels or peripheral vessels) and for the radiation treatment to be delivered. In one embodiment of the present invention, the balloon treatment area length 30 is in a range of approximately 18 mm to 54 mm. For some intervascular gamma radiation treatments, such as treatments on peripheral vessels of the cardiovascular system, the balloon treatment area length 30 may be in a range of approximately 10 mm to 250 mm.

Continuing with reference to FIG. 10, in one embodiment, the radiation source lumen 22 is sealed at its distal end 23 with plug 24 to allow a radiation source 25 to be placed inside the radiation source lumen 22. In another embodiment, the radiation source lumen 22 is left open at its distal end 23 (i.e., it does not have a plug 24) so that a radiation source 25 (placed inside the radiation source lumen 22) can be distally advanced past the multi-lumen balloon 10. Furthermore, not having the radiation source lumen 22 sealed with the plug 24 decreases the stiffness of the multi-lumen balloon even further.

It should be noted that it is not necessary to have a radiation source lumen 22 as part of the multi-lumen balloon centering catheter assembly 1. In some applications, it may be desirable to place the radiation source 25 directly within the central lumen 12 of the balloon 10, without employing a source lumen 22. Not having a radiation source lumen 22 in the balloon central lumen 12 reduces the size of the multi-lumen balloon and decreases the stiffness of the multi-lumen balloon (since the radiation source lumen 22 is a co-extruded shaft), thus allowing the balloon to cross tortuous paths more easily along the body vessel.

The radiation source 25, which may be shaped in the form of a wire, seed, pellets, ribbon, etc., is positioned inside radiation source lumen 22 and is then advanced longitudinally along a prescribed vessel length 16 during patient treatment. In one embodiment of this invention, the multi-lumen balloon centering catheter assembly 1 uses a Phosphorus-32 radiation source as a radiation source 24. However, the multi-lumen balloon of this invention can be used with any radiation source employed in vascular radiotherapy, which includes gamma radiation emitting sources and beta radiation emitting sources known in the art.

Continuing with reference to FIG. 10, two radio-opaque markers, a distal marker 37 and a proximal marker 38, may be attached to the radiation source lumen 22. The radio-opaque markers 37 and 38 are used for positioning the interventional catheter 1 under fluoroscopy, as well as for assisting the stepping (via manual or automatic means) of the radiation source 25 over the entire prescribed region of the vessel 16 to be treated. The markers 37 and 38 are made of any materials known in the art of radio-opaque markers, such as silver, gold, platinum, tungsten, that allow markers to become visible under fluoroscopy. In one embodiment, the radio-opaque markers (37, 38) are attached within the limits of the balloon's treatment area 30. In one configuration, the distal marker 37 is incorporated into the plug 24 of the source lumen 22. In another configuration, radio-opaque markers (37, 38) may be part of a separate device (not shown) that is independent of the balloon catheter assembly.

A soft tip 26 is attached to the distal end 27 of the guidewire lumen 21 to improve trackability and reduce trauma to the body vessel. The length of the soft tip 26 depends on the type of catheter design used, however, the length of the tip is generally in a range of approximately 0.5 mm to 10 mm.

With reference to FIG. 10, the balloon 10 is attached to catheter shaft 41 of the catheter assembly 2. The balloon's proximal seal 29 is attached at a proximal end 44 of flexible catheter shaft 41, near the inflation/deflation port 33. The balloon distal seal 28 is attached to the catheter shaft 41 adjacent to the location where the radiation source lumen 22 ends. In one embodiment, the balloon 10 and assembly 2 are attached by using a laser bond technique. Bonds may also be done using other balloon bonding techniques known in the art, such as thermal or ultrasonic welds, adhesive welds, or other conventional means.

Multi-lumen Balloon Catheter Having a Balloon with Communication Bores between Central and Outer Lumens and a Guidewire Lumen Through the Central Lumen In FIGS. 13–16, a fluted balloon radiation centering catheter assembly 1 for a standard Rapid Exchange catheter with a guidewire lumen extending through the central lumen of a multi-lumen balloon is shown.

Figure 13:
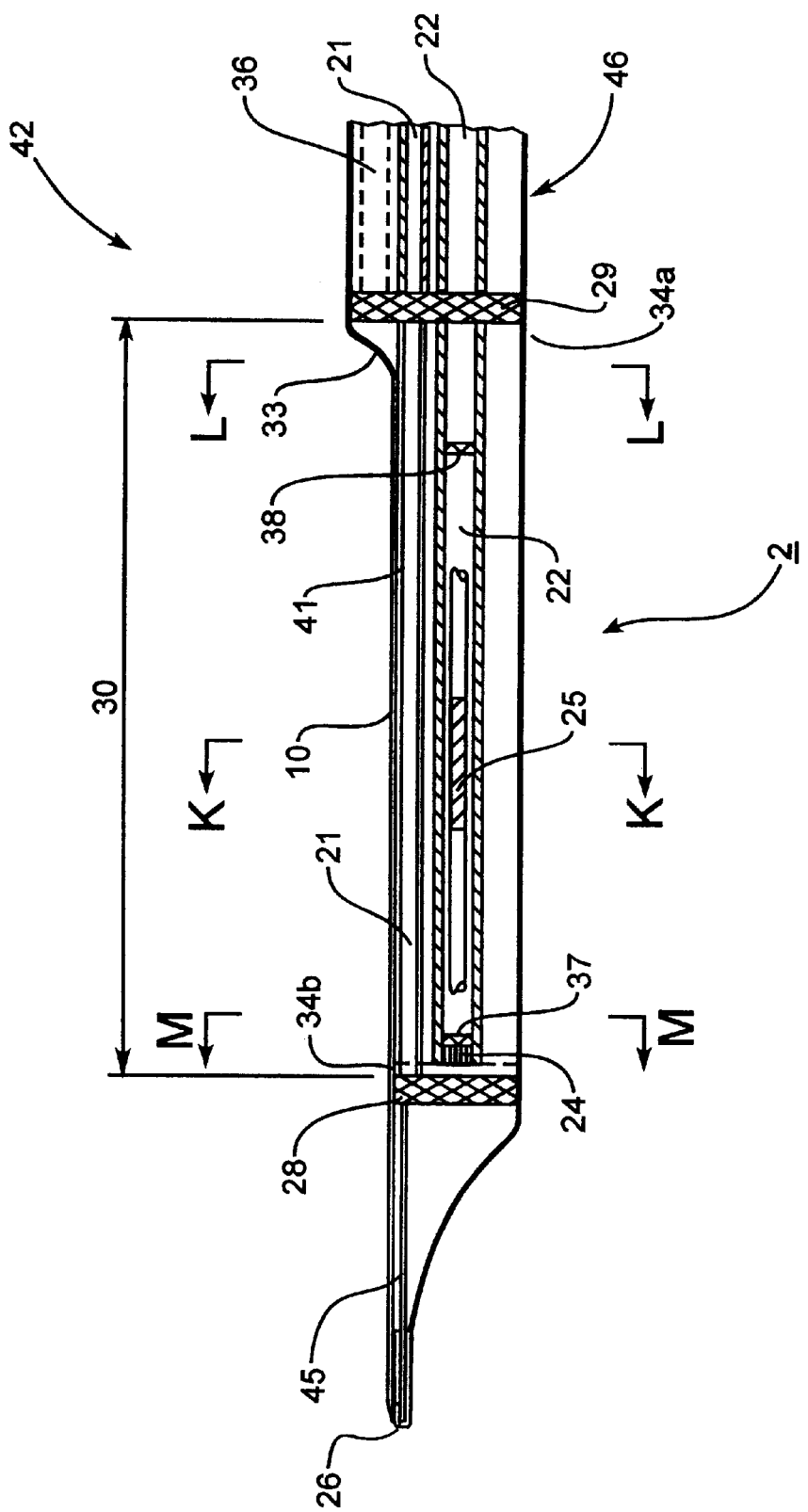
FIG. 13 is a side view of an third embodiment of a multi-lumen fluted balloon catheter assembly (for a standard- RX configuration) for centering a radiation source, where the guidewire lumen and source lumen extend through catheter inner member and central balloon lumen.

Referring to FIG. 13, a multi-lumen fluted balloon radiation centering catheter assembly 1 with the balloon 10 in an inflated state is shown. The fluted balloon radiation centering catheter assembly 1 includes a multi-lumen balloon 10 and an interventional catheter 2. Interventional catheter 2 has a shaft disposed proximate the balloon 10. The balloon 10 includes a plurality of inflatable outer lumens 11 disposed around a central lumen 12, the plurality of outer lumens 11 integrally coupled with the central lumen 12 so as to form the multi-lumen balloon 10. The balloon 10 has a distal seal 28 and a proximal seal 29. Distal seal 28 seals the plurality of distal ends 34b of the balloon outer lumens 11 to the catheter shaft 41 while the proximal seal 29 seals the plurality of proximal ends 34a of the balloon outer lumens 11 to the catheter shaft 41. The distal and proximal seals (28, 29) may each have a width in a range of approximately 0.5 mm to about 5 mm.

Each of the outer lumens 11 takes the form of a "flute" (i.e., an elongated cylinder having tapered ends) when inflated by an inflation medium 18b (shown in FIG. 14 for this balloon catheter assembly). A fluted balloon configuration is shown in FIG. 17, which is a representative illustration of balloon configurations of this invention (as revealed in balloon catheter assemblies of FIGS. 1, 6, 10, and 13).

Continuing with reference to FIG. 13, the catheter shaft includes an inner tubular member 41 having an inner lumen 41a. The catheter shaft further includes a flexible elongate outer tubular member 46. Elongate inner tubular member 41 extends coaxially within the elongate outer tubular member 46.

Referring now to FIG. 14, the balloon central lumen 12 is capable of containing a radiation source 25 (with or without a radiation source lumen 22) therein. The multi-lumen balloon embodiment shown in FIG. 14 is further adapted for receiving a guidewire lumen (with a guidewire 45) through its central lumen 12.

Figure 16:
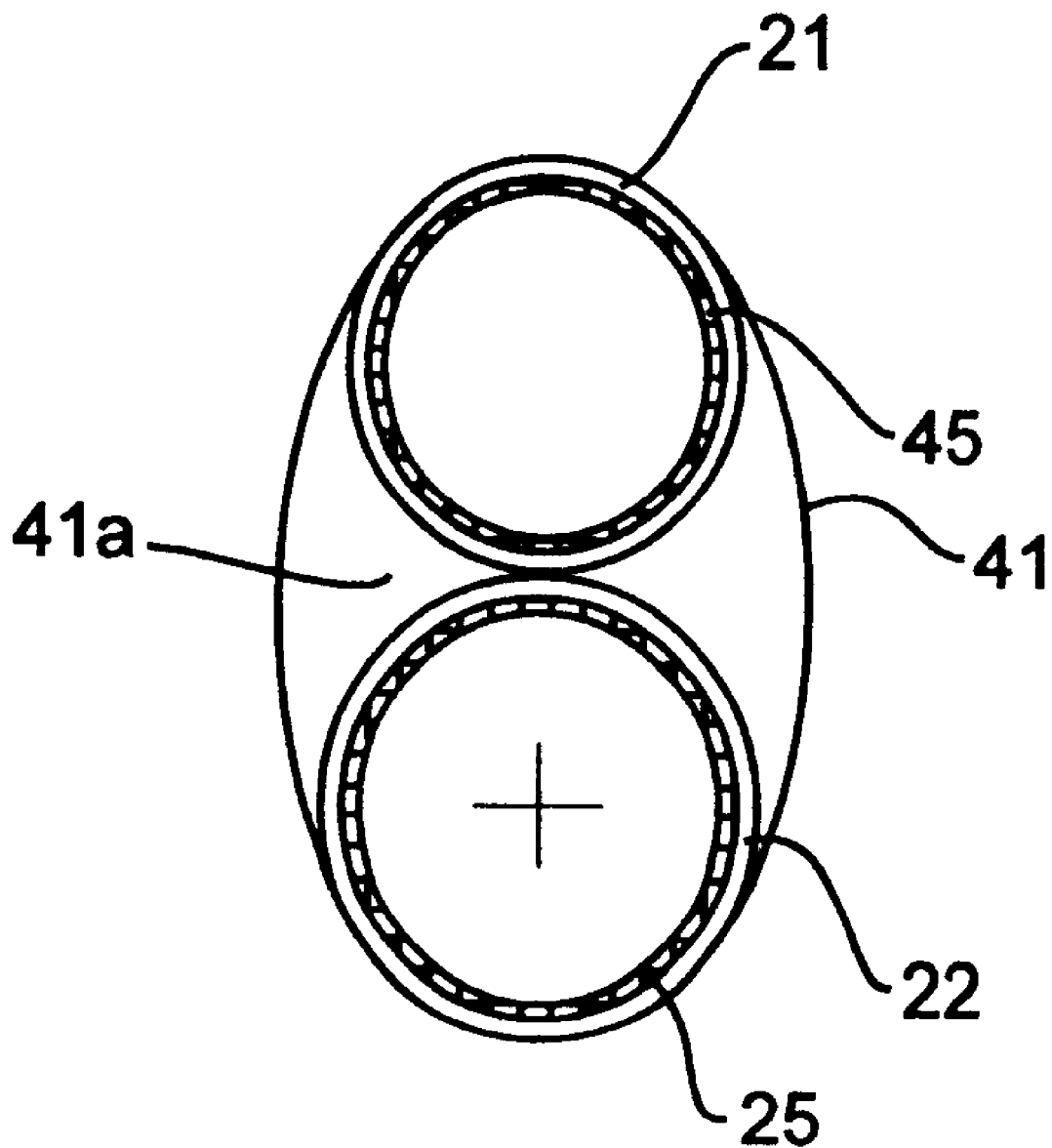
FIG. 16 is a cross-sectional view of the multi-lumen fluted balloon catheter assembly of FIG. 13 taken along line M—M showing guidewire lumen and radiation source lumen.

For the balloon configuration shown in FIG. 14, the balloon 10 includes bores (or channels) 35 that are formed between the outer lumens 11 and the central lumen 12. This arrangement allows an inflation medium 18b to pass from the balloon central lumen 12 into the outer lumens 11 and inflate outer lumens 11, causing a radiation source lumen 22 to be centered within a body vessel 16. In this configuration the central lumen 12 is pressurized in order for the outer lumens 11 to properly inflate and center the radiation source lumen 22 within the body vessel 16. The catheter inner lumen 41a is adapted to serve as an inflation lumen for the balloon central lumen 12 and the outer lumens 11 (as shown in FIG. 16).

Continuing with reference to FIG. 14, when using a standard RX or an over-the-wire radiation catheter type, the radiation source lumen 22 and the guidewire lumen 21 extend longitudinally through the balloon central lumen. The plurality of outer lumens 11 are sealed onto the radiation source lumen 22 and the guidewire lumen 21 for maintaining inflation pressure in the balloon. When inflated by an inflation medium 18b, the balloon outer lumens 11 form flutes positioned parallel to the radiation source lumen 22. During vascular radiotherapy, when inflated and engaged with the walls of the body vessel 16, the balloon outer lumens 11 define a series of straight longitudinal paths 14 that allow for perfusion of blood (not shown) past balloon treatment area 30 (shown in FIG. 13).

The fluted balloon outer lumens 11 can be extruded with either equal diameter 15 (as shown in FIG. 11) or with unequal (or asymmetrical) diameter 15 (as shown in FIG. 14). A balloon arrangement having outer lumens 11 with unequal diameters (for example, a balloon assembly of FIG. 14 with one small "flute" and two large "flutes") is best suited for the "standard RX" or "over-the-wire" catheter designs where the catheter shaft (or inner member) 41 includes two parallel lumens: a source lumen 22 (for a radiation. source 25) and a guidewire lumen 21 (for a guidewire 45). For very small diameter centering balloon catheters, such as the 2 mm diameter balloon catheter designs, the small "flute" 11 shown in FIG. 14 may be eliminated to provide for centering of the radiation source lumen 22.

Continuing with reference to FIG. 14, the diameter 18a of the balloon central lumen 12 is sized based on the radiation source outer diameter and the guidewire lumen outer diameter, for example a radiation source wire having an outer diameter in a range of approximately $10/1000$ in. to $50/1000$ in and a guidewire lumen having an outer diameter in a range of approximately $10/1000$ in. to $15/1000$. The combined balloon diameter 13 (as measured across all balloon outer lumens 11 while balloon is in an inflated or deployed state) is kept in a range of approximately 1.5 mm to 6 mm for coronary vessels and in a range of approximately 3 mm to 12 mm for peripheral vessels. For the embodiment shown in FIG. 14, a balloon having a combined diameter 13 in a range of approximately 1.5 mm to 4 mm is advantageous when treating coronary vessels.

Referring now to FIG. 13, the multi-lumen balloon has a treatment area 30 is defined between the balloon's distal seal 28 and proximal seal 29. The longitudinal length of the balloon treatment area 30 is made to be appropriate for the body vessel to be treated (for example, coronary vessels or peripheral vessels) and for the radiation treatment to be delivered. In one embodiment of the present invention, the balloon treatment area length 30 is in a range of approximately 18 mm to 54 mm. For some intervascular gamma radiation treatments, such as treatments on peripheral vessels of the cardiovascular system, the balloon treatment area length 30 may be in a range of approximately 10 mm to 250 mm.

Continuing with reference to FIG. 13, in one embodiment, the radiation source lumen 22 is sealed at its distal end 23 with plug 24 to allow a radiation source 25 to be placed inside the radiation source lumen 22. In another embodiment, the radiation source lumen 22 is left open at its distal end 23 (i.e., it does not have a plug 24) so that a radiation source 25 (placed inside the radiation source lumen 22) can be distally advanced past the multi-lumen balloon 10. Furthermore, not having the radiation source lumen 22 sealed with the plug 24 decreases the stiffness of the multi-lumen balloon even further.

It should be noted that it is not necessary to have a radiation source lumen 22 as part of the multi-lumen balloon centering catheter assembly 1. In some applications, it may be desirable to place the radiation source 25 directly within the central lumen 12 of the balloon 10; without employing a source lumen 22. Not having a radiation source lumen 22 in the balloon central lumen 12 reduces the size f the multi-lumen balloon and decreases the stiffness of the multi-lumen balloon since the radiation source lumen 22 is a co-extruded shaft), thus allowing the balloon to cross tortuous paths more easily along the body vessel.

The radiation source 25, which may be shaped in the form of a wire, seed, pellets, ribbon, etc., is positioned inside radiation source lumen 22 and is then advanced longitudinally along a prescribed vessel length 16 during patient treatment. In one embodiment of this invention, the multi-lumen balloon centering catheter assembly 1 uses a Phosphorus-32 radiation source as a radiation source 25. However, the multi-lumen balloon of this invention can be used with any radiation source employed in vascular radiotherapy, which includes gamma radiation emitting sources and beta radiation emitting sources known in the art.

Continuing with reference to FIG. 13, two radio-opaque markers, a distal marker 37 and a proximal marker 38, may be attached to the radiation source lumen 22. The radio-opaque markers 37 and 38 are used for positioning the interventional catheter 1 under fluoroscopy, as well as for assisting the stepping (via manual or automatic means) of the radiation source 25 over the entire prescribed region of the vessel 16 to be treated. The markers 37 and 38 are made of any materials known in the art of radio-opaque markers, such as silver, gold, platinum, tungsten, that allow markers to become visible under fluoroscopy In one embodiment, the radio-opaque markers (37, 38) are attached within the limits of the balloon's treatment area 30. In one configuration, the distal marker 37 is incorporated into the plug 24 of the source lumen 22. In another configuration, radio-opaque markers (37, 38) may be part of a separate device (not shown) that is independent of the balloon catheter assembly.

A soft tip 26 is attached to the distal end of the guidewire lumen 21 to improve trackability and reduce trauma to the body vessel. The length of the soft tip 26 depends on the type of catheter design used, however, the length of the tip is generally in a range of approximately 0.5 mm to 10 mm.

With reference to FIG. 13, the balloon 10 is attached to catheter shaft 41 of the catheter assembly 2. The balloon proximal seal 29 is positioned at a proximal end 44 of flexible catheter shaft 41, near the inflation/deflation port 33. The balloon distal seal 28 is positioned to the catheter shaft 41 adjacent to the location where the radiation source lumen 22 ends. In one embodiment, the balloon 10 and assembly 2 are coupled using a laser bond technique. Bonds may also be done using other balloon bonding techniques known in the art, such as thermal or ultrasonic welds, adhesive welds, or other conventional means.

Multi-lumen Balloon Catheter Having a Balloon with or without Communication Bores between Central and Outer Lumens and A Guidewire Longitudinally Extending Outside the Fluted Balloon Lumens In FIGS. 27a–27d, a fluted balloon radiation centering catheter assembly 1 for a catheter with a guidewire longitudinally extending outside the multi-lumen balloon is shown.

Figure 27A:
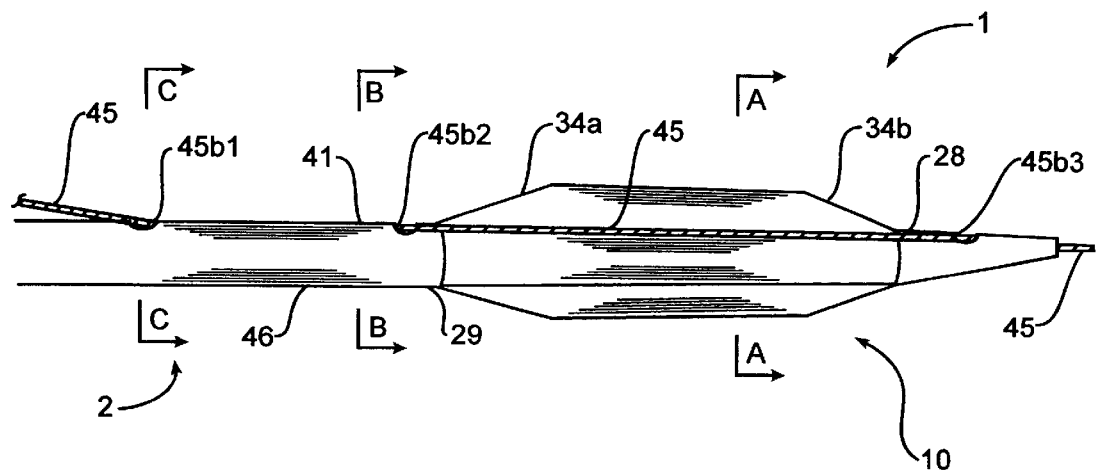
FIG. 27a is a side view of another embodiment of a multi-lumen fluted balloon catheter assembly for centering radiation source, with two additional guidewire exits in the catheter shaft and guidewire extending longitudinally outside the balloon.
Figure 27D:
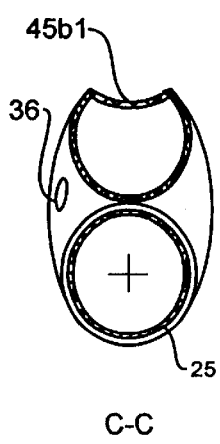
FIG. 27d is a cross-sectional view of the multi-lumen fluted balloon radiation centering catheter assembly of FIG. 27a taken along line C—C.
Figure 27C:
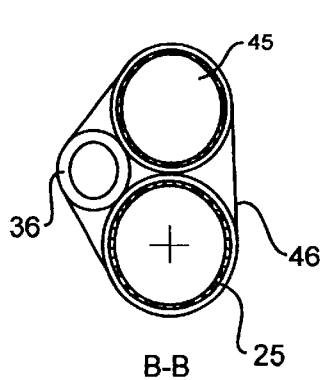
FIG. 27c is a cross-sectional view of the multi-lumen fluted balloon radiation centering catheter assembly of FIG. 27a taken along line B—B.

Referring to FIG. 27a, a multi-lumen fluted balloon radiation centering catheter assembly 1 with the balloon 10 in an inflated state is shown. The fluted balloon radiation centering catheter assembly 1 includes a multi-lumen balloon 10 and an interventional catheter 2. Interventional catheter 2 has a shaft disposed proximate the balloon 10. The balloon 10 includes a plurality of inflatable outer lumens 11 disposed around a central lumen 12, the plurality of outer lumens 11 integrally coupled with the central lumen 12 so as to form the multi-lumen balloon 10. The balloon 10 has a distal seal 28 and a proximal seal 29. Distal seal 28 seals the plurality of distal ends 34b of the balloon outer lumens 11 to the catheter shaft 41 while the proximal seal 29 seals the plurality of proximal ends 34a of the balloon outer lumens 11 to the catheter shaft 41. The distal and proximal seals (28, 29) may each have a width in a range of approximately 0.5 mm to about 5 mm.

Each of the outer lumens 11 takes the form of a "flute" (i.e., an elongated cylinder having tapered ends) when inflated by an inflation medium 18b (shown in FIG. 14 for this balloon catheter assembly). A fluted balloon configuration is shown in FIG. 17, which is a representative illustration of balloon configurations of this invention (as revealed in balloon catheter assemblies of FIGS. 1, 6, 10, 13 and 27a).

Figure 27B:
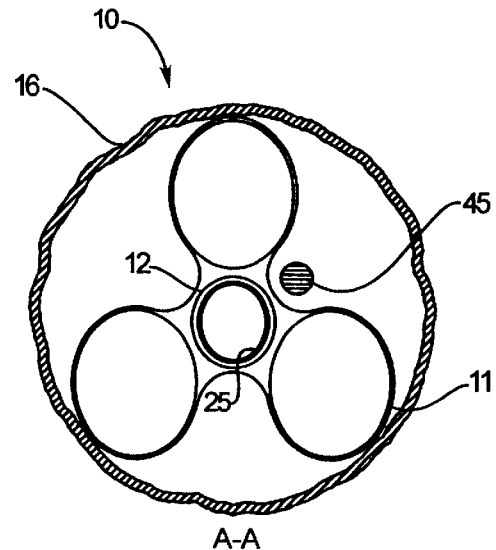
FIG. 27b is a cross-sectional view of the multi-lumen fluted balloon radiation centering catheter assembly of FIG. 27a taken along line A—A.

Continuing with reference to FIG. 27a, the catheter shaft includes an inner tubular member 41 having an inner lumen 41a (shown in FIG. 27b). The catheter shaft 41 further includes a flexible elongate outer tubular member 46. Elongate inner tubular member 41 extends coaxially within the elongate outer tubular member 46.

Still referring to FIG. 27a, two additional guidewire exits (45b1 and 45b2) are notched (or cut out) along the catheter shaft (which includes the tubular member 41) to permit a guidewire 45 to extend lengthwise outside the multi-lumen balloon 10 (see FIG. 27b) from an existing guidewire exit notch 45b3 to a guidewire exit notch 45b2. At the point of the guidewire exit notch 45b2, the guidewire 45 enters the catheter shaft' tubular member 41, extends lengthwise through a portion of the shaft and then exits the shaft at the second guidewire exit notch 45b11. The profile of the fluted balloon with standard RX configuration is $59/1000$ in. by $60/1000$ in., while the profile of the fluted balloon without the guidewire lumen is about $51/1000$ in.

Through this balloon catheter embodiment, the guidewire riding length is extended over the "tip RX" design. This design arrangement has a number of benefits over prior art designs, including (a) maintaining the multi-lumen balloon profile for the "standard RX" design, (b) reducing the profile of the balloon proximal seal, (c) allowing the bore communication between the central lumen and the plurality of outer lumens for an improved centering of the radiation source, and (d) reduces radial shielding effect.

Balloon Treatment Area Markers

As described and shown in figures above, the multi-lumen balloon catheters of this invention may include radio-opaque markers for positioning the interventional catheter 1 under fluoroscopy, as well as for assisting the stepping (via manual or automatic means) of the radiation source 25 over the entire prescribed region of the vessel 16 to be treated. Generally, the markers include a distal marker 37 and a proximal marker 38. Markers 37 and 38 may be attached to the radiation source lumen 22 by adhesive bonding. Markers may also be swaged onto the radiation source lumen.

In yet another embodiment, markers 37 and 38 may be attached directly onto the fluted balloon using a sputtering or vapor deposition process. In this process, a marker material such as gold is deposited onto the balloon using any sputtering or vapor deposition techniques known in the field. It should be noted that the marker material deposition is not limited to a specific area of the multi-lumen balloon; the marker material may be deposited onto the central lumen of the balloon, around the entire circumference of the multi-lumen balloon, or any other balloon area desired.

The markers 37 and 38 may made of any materials known in the art of radio-opaque markers, such as silver, gold, platinum, tungsten, that allow markers to become visible under fluoroscopy. In one embodiment, the radio-opaque markers (37, 38) are attached within the limits of the balloon's treatment area 30.

Balloon Proximal Seal

A unique proximal seal geometry used to seal a multi-lumen fluted balloon to a catheter shaft and method for manufacturing same is described. In one embodiment (described herein), the proximal seal geometry is used to seal a four-lumen fluted balloon to a shaft containing both a radiation source lumen and a guidewire lumen. In another embodiment (not shown), where the radiation source is used without a radiation source lumen, the proximal seal geometry is used to seal a four-lumen fluted balloon to a shaft containing only a guidewire lumen. In yet another embodiment (not shown), where the catheter type is a "tip RX" (i.e., the guidewire lumen does not pass through any of the balloon lumens), the proximal seal geometry is used to seal a four-lumen fluted balloon to a shaft containing only a radiation source lumen.

Referring to FIG. 18, a cross sectional view of a multi-lumen fluted balloon 10 for treating a body vessel 16 in the vascular system is shown. Balloon 10 includes a central lumen 12 and a plurality of outer lumens (or lobes) 11 disposed around the central lumen 12. The outer lumens 1 1 are integrally coupled with the central lumen 12 so as to form the multi-lumen balloon 10. Each of the balloon outer lumens 11 has an inner radial length (or diameter) 18 and an outer diameter 15, defining balloon outer lumen walls 17. The walls 17 of balloon outer lumens 11 are made very thin to allow proper inflation and deflation of outer lumens 11.

The multi-lumen balloon 10 is manufactured of balloon materials, such as Pebax™, nylon, polyethylene, polyurethane, or polyester. Materials for use in fabricating the multi-lumen balloon 10 of the present invention are selected by considering the properties and characteristics (e.g., softness, durability, low stiffness) required by angioplasty balloons, as well as considering properties necessary for successful balloon fabrication (e.g., balloon material compatible with other catheter materials and bonding process, material extruding well, etc.).

In the embodiment illustrated in FIG. 17, a radiation source lumen 22 is placed into the central lumen 12 of the fluted multi-lumen balloon 10, the radiation source lumen 22 extending lengthwise through the central lumen 12. A guidewire lumen 21 is also placed into one of the balloon's outer lumens 11 (third outer lumen 11 of the balloon is hidden in FIG. 17), the guidewire lumen 21 extending lengthwise through the balloon outer lumen. The balloon outer lumen 11 containing the guidewire lumen 21 is labeled the guidewire outer lumen. Both the radiation source lumen 22 and the guidewire lumen 21 are manufactured as co-extrusions having an inner layer made of a material such as polyethylene and an outer layer made of a material such as Pebax, nylon, or Primacor.

A first mandrel 22a is then inserted through the radiation source lumen 22 and a second mandrel 21a is inserted:through the guidewire lumen 21. It should be noted that if the catheter type does not require for a guidewire lumen 21 to extend through the multi-lumen balloon (for example, a "tip RX" catheter type or a catheter assembly having slideable distal and proximal seals, as discussed above), the second mandrel 21a may not be necessary and would not have to be inserted through one of the balloon outer lumens 11. For balloon catheter embodiments where a radiation source lumen is not used (i.e., a radiation source would be positioned directly within the balloon central lumen during the intervascular radiotherapy procedure), the first mandrel 22a may be inserted directly through the balloon central lumen 12.

Figure 19A:
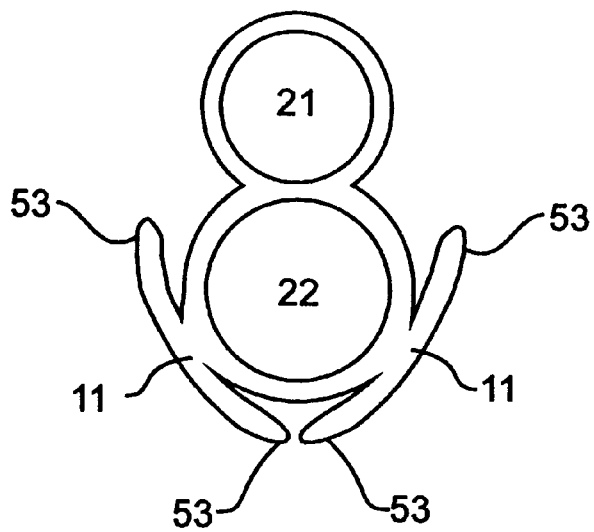
FIG. 19a is a cross-sectional view of the four-lumen balloon for a centering catheter assembly with two balloon outer lumens flattened for proximal balloon seal preparation.

After the first mandrel 22a is inserted through the radiation source lumen 22 and the second mandrel 21a is inserted through the guidewire lumen 21, the two outer lumens 11 not occupied by the guidewire lumen 21 are compressed so as to give the outer lumens 11 (and thus the balloon proximal seal) a more compact configuration. Note that FIG. 18 shows a cross-section of the outer lumens 11 shape before the outer lumens are compressed. As part of the compressing operation, the proximal ends of the two outer lumens 11 are flattened (see FIG. 19a), thus forming flattened outer lumens.

Figure 19B:
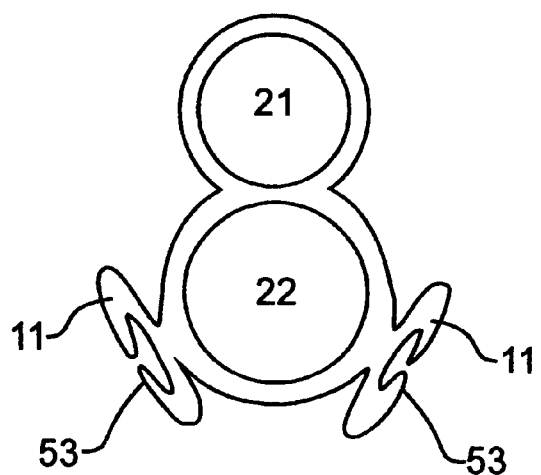
FIG. 19b is a cross-sectional view of the four-lumen balloon for a centering catheter assembly with a configuration for folding the two balloon outer lumens flattened for balloon proximal seal preparation.

If a more packed configuration is desired for the flattened outer lumens 11, the ends 53 of the flattened outer lumens 11 are folded back over themselves (see FIG. 19c), thus creating folded outer lumens. It is necessary to fold the ends 53 of the flattened outer lumens 11 back over themselves to ensure that there is enough balloon material outside of the inflation lumens 54b, 55b (shown in FIG. 20a, and discussed in more detail below) of the outer lumens 11 to maintain the inflation pressure. Alternative folding patterns of the flattened outer lumens may also be used if there is ample thickness in the catheter outer member 46 to ensure that the inflation lumens (54b, 55b) will not leak. In one approach, the flattened outer lumens 11 may be left in the flattened profile shown in FIG. 19a or both ends 53 of the outer lumens may be folded towards the guidewire outer lumen (i.e., the outer lumen 11 containing the guidewire lumen 21) (see FIG. 19b). Folding the flattened outer lumens 11 may be performed manually, using full automation techniques, or using a combination of manual and automated sub-steps.

Figure 19C:
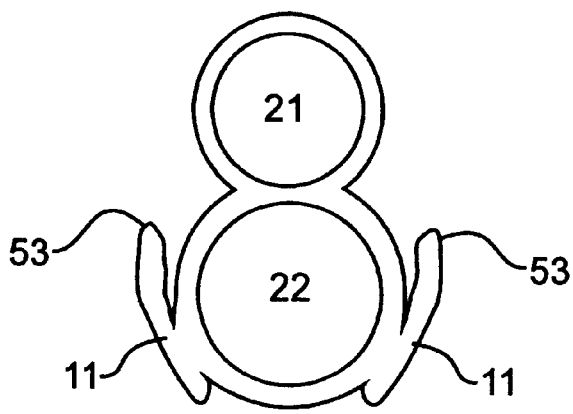
FIG. 19c is a cross-sectional view of the four-lumen balloon for a centering catheter assembly with another configuration for folding the two balloon outer lumens flattened for balloon proximal seal preparation.

If the flattened outer lumens are folded manually, many different approaches may be taken. For example, to achieve the embodiment shown in FIG. 19b, the flattened outer lumens are folded by simply using the thumb and forefinger to push down (or up, depending on the up or down orientation of the guidewire outer lumen) the two flattened outer lumens. The embodiment shown in FIG. 19c is done by using a pair of tweezers to fold over the ends of each of the two flattened outer lumens (one side at the time) until the desired fold configuration is achieved.

After folding the flattened balloon outer lumens 11, a catheter outer member 46 is placed over the central lumen 12 (with radiation source lumen 22) and the guidewire outer lumen 11 (with the guidewire lumen 21). The catheter outer member 46 also overlaps the two outer lumens 11 of the multi-lumen balloon 10 not occupied by the guidewire lumen 21. The catheter outer member 46 may be manufactured from materials such as nylon, Pebax, polyurethane, etc.

Inflation lumen mandrels 54a and 55a are then inserted to form and maintain individual lumens (54b, 55b) for inflation of the outer lumens 11. The inflation lumen mandrels (54a, 55a) are generally inserted from the balloon distal end 28 (see FIG. 17), however, the insertion of the inflation lumen mandrels may also be accomplished from the balloon proximal end 29.

The inflation lumen mandrels 54a (shown in FIG. 20d) have a "football"-shape cross-section 54aa to better contour with the shape of the outer member 46 and prevent leaking of the inflation medium 18 through the inflation lumens 54a. In current prior art balloon seal processes, which use mandrels having a straight edged configuration (such as a flattened round wire mandrel), seal leaking can occur because the "sharp" edges of the flattened round wire mandrels protrude out of the seal, thus causing the inflation medium to leak out of the seal.

Referring to FIG. 20d, the inflation lumen mandrels 54a include a shaft 54a1 having a substantially football-shaped cross section. The shaft 54a1 has a solid center, however, it may also have a hollow center 54a2 extending lengthwise therein. The "football" shaped inflation lumen mandrels 54a are also symmetrical (i.e., they do not have a "front", "back", "top", or a "bottom") to eliminate any dependence on a specific orientation and for ease of use during the manufacture of the proximal seal. The dimensions (i.e., length and cross-section "diameter") of the inflation lumen mandrels 54a vary depending for example, on the diameter of the balloon lumens, the type of material the mandrel is made of, etc.

Referring to FIGS. 20a–20c, FIG. 20a shows a cross-section view of the completed balloon proximal seal showing the inflation lumens 54b created by the "football" shaped inflation lumen mandrels 54a for the two outer lumens not occupied by the guidewire lumen, and the inflation lumen 55b created by the flattened round wire inflation lumen mandrel 55a for the guidewire lumen 21. The flattened round wire inflation lumen mandrel 55a can be replaced with a "football" shaped inflation mandrel 56a (see FIG. 20b) or a triangular shaped mandrel 56b (see FIG. 20c). Following the insertion of the first and second mandrels (21a, 22a) to retain the radiation source lumen 22 and the guidewire lumen 21, and the inflation lumen mandrels (54a, 55a) to retain the inflation lumens (54b, 55b), the proximal end of the multi-lumen fluted balloon 10 is bonded to the distal end of the catheter outer lumen 46.

For the embodiment shown in FIG. 20a, a square-wave laser pattern bond is used to bond the outer member 46 to the balloon 10. A heat shrink tube 57b (shown in FIG. 21c) is temporarily used during the square-wave laser bond process. The heat shrink tube 57b is positioned over the balloon catheter "proximal seal assembly", which includes the proximal end of the multi-lumen balloon (with the radiation source lumen and the guidewire lumen if catheter assembly so requires it), the distal end of the catheter outer member, and all the mandrels. When heat from the laser beam is applied onto the heat shrink tube 57b, the tube compresses radially onto the balloon catheter proximal seal assembly. The shrink tube compression causes the materials of the balloon proximal end and the outer member distal end to closely fuse together, creating a leak-tight balloon proximal seal. The heat shrink tube is then removed. It should be noted that the heat shrink tubing may be substituted with heat shrink materials having other shapes, such as heat shrink sheaths, etc.

The shrink tubing is made from materials known in the art of catheter balloon manufacture. For one embodiment, the shrink tubing has a diameter 57b1 of 2.5 mm, however, the diameter 57b1 of the shrink tubing to be used depends on a number of factors, such as the size of the balloon catheter to be manufactured, the degree of folding performed on the balloon outer lumens, whether the balloon catheter includes a radiation source lumen and/or a guidewire lumen extending through the balloon, etc.

In the present invention, laser bonding techniques, such as laser bonding using a square-wave laser pattern (or design) are desired. However, bonds may also be done using other balloon bonding techniques known in the art, such as thermal bonding, ultrasonic bonding, adhesive bonding (for example using a glue-type material), or other conventional means.

Following the laser bonding of the outer member 46 to the balloon 10, the inflation lumen mandrels 54a and 55a are removed from the balloon proximal seal assembly.

Given the "egg-shape" like configuration, the completed balloon proximal seal cross-section may have a "small diameter" 46d1 (i.e., measured horizontally across the seal) in the range of approximately 35–50 mm, while the "large diameter" 46d2 (i.e., measured vertically across the seal) in the range of approximately 60–80 mm. In one embodiment, the proximal seal cross section has a "small diameter" 46d1 of about 47 mm and a "large diameter" 46d2 of about 62 mm.

"Football"-shaped Mandrels

As mentioned above, "football"-shaped mandrels are used in the manufacture of the multi-lumen balloon centering catheter proximal seal. Mandrels having a "football"-shape cross-section are not just limited to the manufacture of centering catheters. "Football"-shape cross section mandrels can also be used in fabricating other medical interventional devices, such as atherectomy devices, delivery systems (stent or drug) and other devices requiring a tight seal configuration.

Referring to FIG. 20d, a "football"-shape cross section mandrel includes a shaft 54a1 having a substantially football-shaped cross section. The shaft 54a1 has a solid center, however, it may also have a hollow center 54a2 extending lengthwise therein. The "football"-shaped mandrel shaft 54a1 is made to be symmetrical (i.e., the shaft does not have a "front", "back", "top", or a "bottom") to eliminate any dependence on a specific orientation and for ease of use. The "football"-shaped mandrel 54a may be manufactured out of metal, of a non-stick material such as Teflon, or of any non-metal materials that will not melt at the same temperature as the materials used for manufacturing the particular medical device. The dimensions (i.e., length and cross-section "diameter") of the "football"-shaped mandrel 54a vary depending for example, on the diameter of the balloon lumens, the type of material the mandrel is made of, etc. In one embodiment, the "football"-shaped mandrel 54a has a "large diameter" 54aa1 (see FIG. 20d) in a range of approximately $4/1000$–$30/1000$ in. to a "small diameter" 54aa2 in a range of approximately $2/1000$–$20/1000$ in.

Balloon Distal Seal

A unique balloon distal seal geometry used to seal a multi-lumen fluted balloon to a catheter shaft is described. The present invention provides a solution to the problem of bundling together a multi-lumen shaft at the distal end of a multi-lumen balloon without using additional materials that could increase the stiffness of the distal tip. The balloon distal seal is completed following the completion of the balloon proximal seal (as discussed above).

In one embodiment (described herein), the balloon distal seal geometry is used to seal a four-lumen fluted balloon to a shaft containing both a radiation source lumen and a guidewire lumen extending through the balloon lumens. It should be noted that for a "tip RX" catheter type (i.e., where the guidewire lumen does not extend through any of the balloon lumens), the balloon distal seal geometry is used to seal a four-lumen fluted balloon to a shaft containing a radiation source lumen and a short guidewire lumen distally positioned to the multi-lumen balloon. In another embodiment (not shown), where the radiation source is used without a radiation source lumen, the balloon distal seal geometry is used to seal a four-lumen fluted balloon to a shaft containing only a guidewire lumen.

Referring to FIG. 18, a cross sectional view of a multi-lumen fluted balloon 10 for treating a body vessel 16 in the vascular system is shown. Balloon 10 includes a central lumen 12 and a plurality of outer lumens (or lobes) 11 disposed around the central lumen 12. The outer lumens 11 are integrally coupled with the central lumen 12 so as to form the multi-lumen balloon 10. The multi-lumen balloon 10 is manufactured of balloon materials, such as Pebax™, nylon, polyethylene, polyurethane, or polyester.

Referring to FIG. 17, a radiation source lumen 22 is placed into the central lumen 12 of the fluted multi-lumen balloon 10, the radiation source lumen 22 extending lengthwise through the central lumen 12. A guidewire lumen 21 is also placed into one of the balloon's outer lumens 11 (third outer lumen 11 of the balloon is hidden in FIG. 17), the guidewire lumen 21 extending lengthwise through the balloon outer lumen. The balloon outer lumen 11 containing the guidewire lumen 21 is labeled the guidewire outer lumen. Both the radiation source lumen 22 and the guidewire lumen 21 are manufactured as co-extrusions having an inner layer made of a material such as polyethylene and an outer layer made of a material such as Pebax, nylon, or Primacor.

Figure 21A:
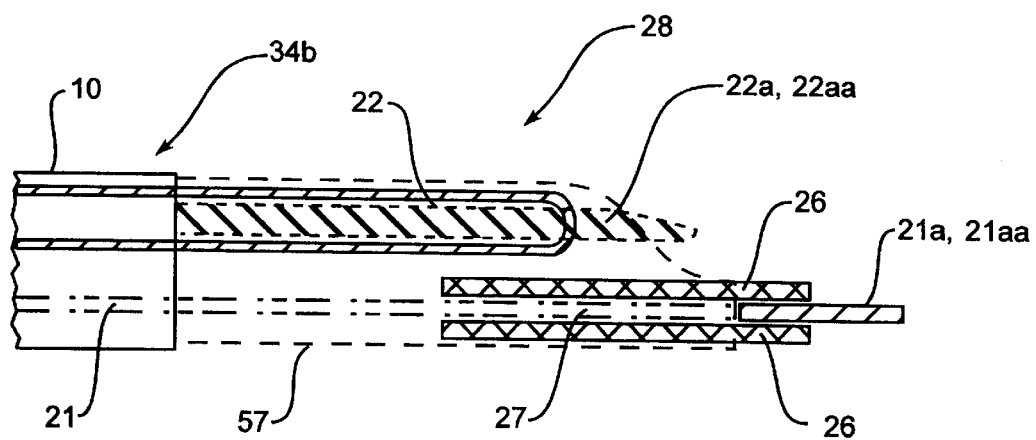
FIG. 21a is a schematic side view of the distal balloon seal area for the multi-lumen fluted balloon radiation centering catheter assembly of FIG. 1.

Referring to FIG. 21a, a completed balloon distal seal 28 is illustrated. As discussed above, the balloon distal seal is completed following the completion of the balloon proximal seal.

To complete the distal seal 28 for a multi-lumen balloon radiation centering catheter, the following sub-steps are performed. First, a first source mandrel 22a is inserted into the radiation source lumen 22 and a first guidewire mandrel 21a is inserted into the guidewire lumen 21. Mandrels 22a and 21a form a first set of source and guidewire mandrels. In one embodiment of this invention, the first source mandrel 22a has a diameter of 0.0225 in., while the first guidewire mandrel 21a has a diameter of 0.017 in. The diameters of the first source and guidewire mandrels may vary depending on a number of factors, such as the type of source used, the size of the multi-lumen balloon when inflated (e.g., 2 mm, 3 mm balloon overall diameter), etc.

Next, a soft tip material 26 is placed over the first guidewire mandrel 21a so as to overlap the guidewire lumen 21. The soft tip material 26 is attached to the distal end 27 of the guidewire lumen 21 to improve trackability and reduce trauma to the body vessel. The length of the soft tip 26 depends. on the. type of catheter design used. However, when completed, the length of the soft tip 26 is generally in a range of approximately 0.5 mm to 10 mm. The soft tip is manufactured from materials generally known in the field of balloon angioplasty.

Next, to prepare the balloon distal seal for laser bonding, a first shrinkable material, such as a shrink tube 57b is positioned over the balloon distal seal sub-assembly. The sub-assembly includes the distal end of the multi-lumen balloon (with the radiation source lumen and the guidewire lumen, if catheter assembly so requires it) and both mandrels (21a, 22a). The distal seal sub-assembly is then fastened using a hot box device (not shown). The balloon distal end 34b is then sealed using a laser device (not shown). It should be noted that the heat shrink tube 57b is only temporarily used during the laser bond process.

When heat from the laser beam is applied onto the heat shrink tube, the tube compresses radially onto the balloon catheter distal seal assembly. The shrink tube compression causes the materials of the balloon distal end 34b to closely fuse together, creating a leak-tight balloon distal seal. The heat shrink tube 57b is then removed.

It should be noted that the heat shrink tube may be substituted with heat shrink materials having other shapes, such as heat shrink sheaths, etc. The shrink tube 57b is made from materials known in the art of catheter balloon manufacture. For one embodiment, the shrink tube 57b has a diameter 57b1 of 2.5 mm, however, the diameter of the shrink tube to be used depends on a number of factors, such as the size of the balloon catheter to be manufactured, the degree of folding performed on the balloon outer lumens, whether the balloon catheter includes a radiation source lumen and/or a guidewire lumen extending through the balloon, etc.

After removing the first shrink tube 57b, a tip jacket 57 is placed over both the guidewire lumen 21 and radiation source lumen 22. A second shrinkable material, such as a shrink tube 57c is placed over the tip jacket 57. The second shrink tube 57c is made from materials known in the art of catheter balloon manufacture. For one embodiment, the shrink tubing 57c has a diameter 57b1 of 2.0 mm, however, the diameter may range in a range of approximately 1.0–3.0 mm. The distal seal sub-assembly (with the tip jacket 57) is then sealed using a laser device (not shown).

The multi-lumen fluted balloon distal seal sub-assembly is laser sealed using a conventional helical-wave laser design. In the present invention, laser sealing or bonding techniques such as the square-wave laser design may be desirable. However, bonds may also be done using other balloon bonding techniques known in the art, such as thermal or ultrasonic welds, adhesive bonds (for example glue), or other conventional means.

Following the laser bonding of;the tip jacket 57, the second shrink tubing 57c is removed. The first set of source and guidewire mandrels (22a, 21a) is then replaced with a second set of source and guidewire mandrels (22aa, 21aa) having smaller diameters than mandrels 22a and 21a. In one embodiment of this invention, the second source mandrel 22aa has a diameter of 0.0205 in., while the second guidewire mandrel 21aa has a diameter of 0.016 in. The diameters of the second source and guidewire mandrels may vary depending on a number of factors, such as the type of source used, the size of the multi-lumen balloon when inflated (e.g., 2 mm, 3 mm balloon overall diameter), etc.

Figure 21B:
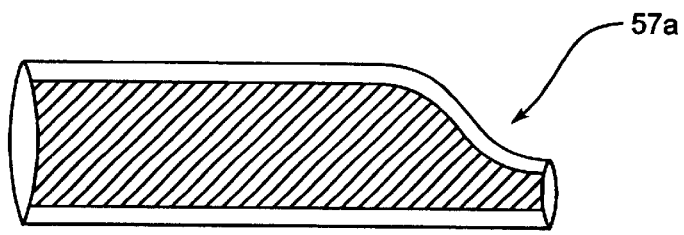
FIG. 21b is a schematic side view of the tip-forming sheath for forming the tip of balloon distal seal for the multi-lumen fluted balloon radiation centering catheter assembly of FIG. 1.
Figure 21C:
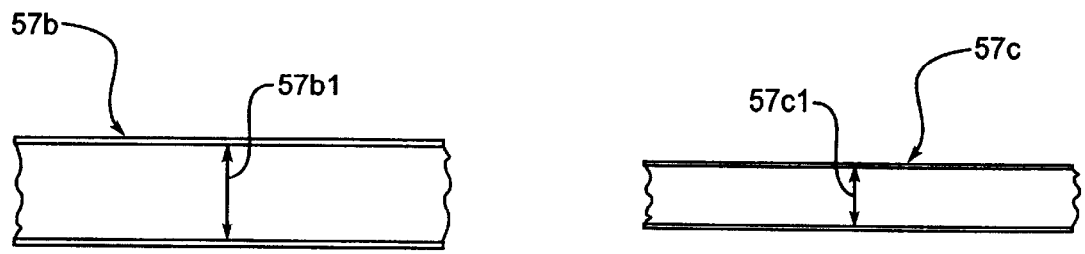
FIG. 21c is a schematic side view of the first and second heat shrink tube materials used for the balloon distal seal.

Once the source and guidewire mandrels are replaced with smaller-diameter mandrels, a tip-forming sheath 57a (shown in FIG. 21b) is placed over the laser-sealed tip jacket 57. Using the tip-forming sheath 57a, a guidewire soft tip (shown in FIGS. 1, 6, 10, and 13) is formed using by placing the balloon seal sub-assembly into a hot box (not shown). At the completion of the distal seal 28, the second source mandrel 22aa and the second guidewire mandrel 21aa are removed from the balloon seal sub-assembly.

Alternative Source Mandrel Designs for Distal Seal

The source mandrels presented above refer to a mandrel design having a circular cross-section. However, the circular cross-section design for the source mandrels may be substituted by using two additional source mandrel designs: (1) a tapered-shape mandrel, and (2) a ramped-shape mandrel. These two embodiments of this invention are now discussed

Tapered Mandrel

Figure 21D:
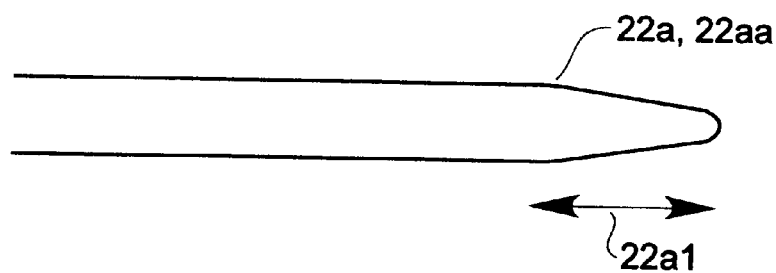
FIG. 21d is a schematic side view of the source mandrel having a tapered length.

Referring to FIG. 21d, a tapered mandrel is formed by having a gradual taper of one end of the mandrel (22a or 22aa) while keeping the round cross-sectional shape concentric to the mandrel. The tapered mandrel has a gradual taper length 21a1 that may vary from 0 cm (i.e., flat ended mandrel) to a taper length 21a1 of 10 cm. This gradual taper shapes the end of the source lumen 22 to direct the radiation source (such as a wire) directly at center of the lumen.

Ramped Mandrel

Figure 21E:
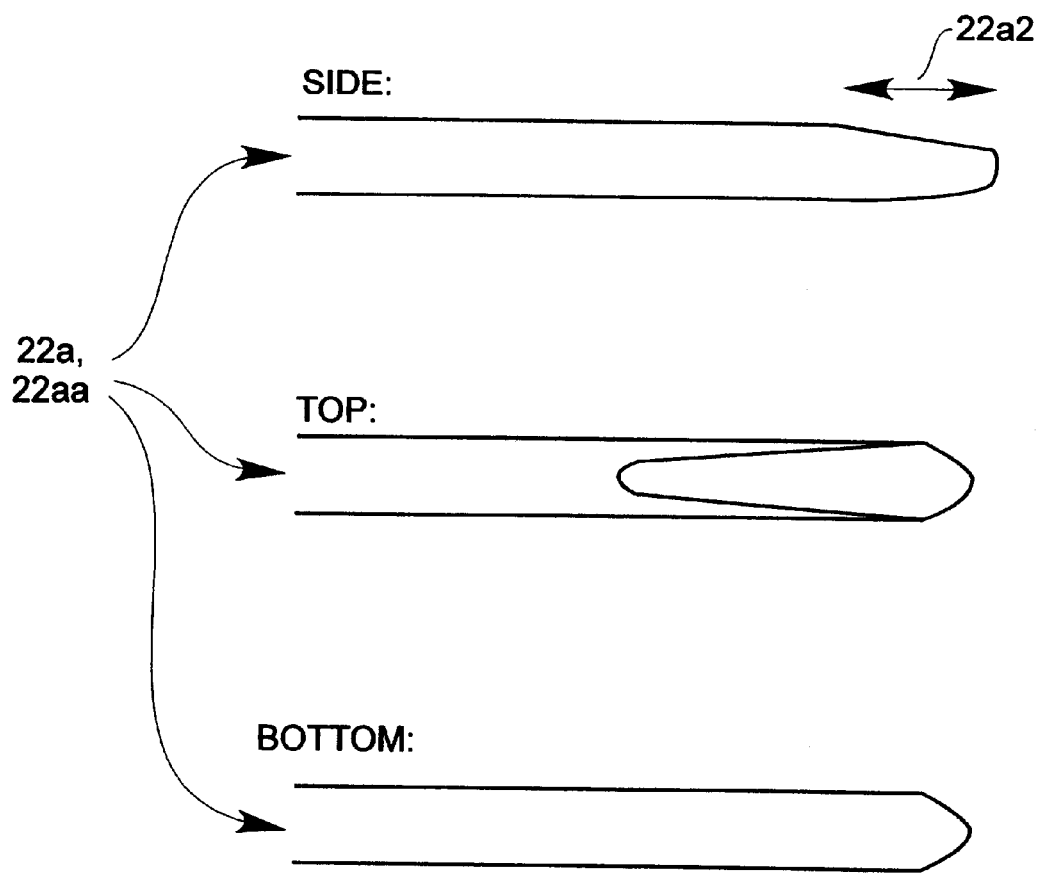
FIG. 21e shows schematic side, top and bottom views of the source mandrel having a ramp length.

Referring to FIG. 21e, a ramped mandrel (22a or 22aa) is shown. In the ramped mandrel design, a round is first made to one end of the mandrel. Then a flat ramp is cut into the same end of the mandrel on one side (see FIG. 21e). The ramped mandrel has a ramp length 22a2 that may vary from 0 cm (i.e., flat ended mandrel) to a ramp length 22a2 of 5 cm. This ramped feature shapes the end of the source lumen to direct the source wire slightly downwards and away from exiting through the top of the lumen.

Method of Manufacture
Multi-Lumen Tubing

Referring to FIGS. 22a–25a, the multi-lumen fluted balloon 10 of this invention is fabricated by blowing a multi-lumen tubing 60 created using an extrusion process. The multi-lumen extruded tubing 60 has a tubing body 61, a central lumen 62, and at least one outer lumen 63 disposed adjacent to the central lumen 62. Generally, a plurality of outer lumens 63 are disposed adjacent to the central lumen 62. The outer lumen 63 is coupled with the central lumen 62 by a shared wall 67 (as shown in FIGS. 22a–25a). In one embodiment, the multi-lumen tubing 60 has three outer lumens 63 disposed adjacent to the central lumen 62.

Referring the FIGS. 23a and 24a, in one embodiment of the present invention, the multi-lumen tubing 60 has at least one outer lumen 63 disposed adjacent to the central lumen 62. The outer lumen 63 is coupled with the central lumen 62 by a shared wall 67. The multi-lumen tubing 60 further includes an undercut radius region 65 disposed between the central lumen 62 and the outer lumen 63. The shared wall 67 may have a shared wall thickness 67b in the range of approximately 50%–200% of the outer lumen wall thickness 67c (as shown in FIG. 23a). In one embodiment, the shared wall 67 may have a shared wall thickness 67b in the range of approximately 80%–120% of the outer lumen wall thickness 67c (as shown in FIG. 24a).

Referring to FIG. 22a, in another embodiment of the present invention, the multi-lumen tubing 60 has at least one outer lumen 63 disposed adjacent to the central lumen 62. The outer lumen 63 is coupled with the central lumen 62 by a shared wall 67. The multi-lumen tubing 60 includes a fillet radius region 66 instead of the undercut region 65 shown in the embodiments of FIGS. 23a and 24a. The fillet radius region 66 is disposed between the central lumen 62 and the outer lumens 63. The shared wall 67 may have a shared wall thickness 67b in the range of approximately 50%–200% of the outer lumen wall thickness 67c. In one embodiment, the shared wall 67 may have a shared wall thickness 67b in the range of approximately 80%–120% of the outer lumen wall thickness 67c (as shown in FIG. 23a).

Referring to FIG. 25a, in a third embodiment of the present invention, the multi-lumen tubing 60 includes a standoff region 64 disposed between the central lumen 62 and the outer lumens 63. In this configuration, the standoff region 64 is the same as the shared wall 67 (i.e., the standoff region 64 has the same shape and length as the shared wall 67). The standoff region 64 may have a standoff region thickness 67bb in the range of approximately 50%–200% of the outer lumen wall thickness 67c. In one embodiment, the standoff region 64 may have a standoff region thickness 67bb in the range of approximately 80%–120% of the outer lumen wall thickness 67c (as shown in FIG. 25a).

The multi-lumen tubing 60 of the present invention may have an overall diameter 68 in the range of approximately $20/1000$ in. and $50/1000$ in. In one embodiment of this invention, the multi-lumen tubing 60 may have an overall diameter 68 in a range of approximately about $34/1000$ in. to $48/1000$ in.

The central lumen 62 of the multi-lumen tubing 60 may have an inner diameter (69a-69d, as shown in FIGS. 22a–25d) in a range of approximately about $7/1000$ in. to $13/1000$ in. In one embodiment of this invention, the central lumen 62 of the multi-lumen tubing 60 has an inner diameter of about $10/1000$ in.

The outer lumens 63 of the multi-lumen tubing 60 may have an outer lumen wall thickness 67c in a range of approximately $2/1000$ in. to $8/1000$ in. In one embodiment of this invention, the outer lumens 63 may have an outer lumen wall thickness 67c in a range of approximately $3.5/1000$ in. to $5/1000$ in.

The multi-lumen tubing 60 is manufactured using balloon materials, such as resin, Pebax™, nylon, polyethylene, polyurethane, or polyester. Materials for use in fabricating the. multi-lumen extrusion tubing 60 of the present invention are selected by considering the properties and characteristics (e.g., softness, durability, low stiffness) required by angioplasty balloons, as well as considering properties necessary for successful balloon fabrication (e.g., balloon material compatible with other catheter materials and bonding process, material extruding well, etc.).

Multi-Lumen Tubing—Method of Manufacture: Extrusion

Figure 26:
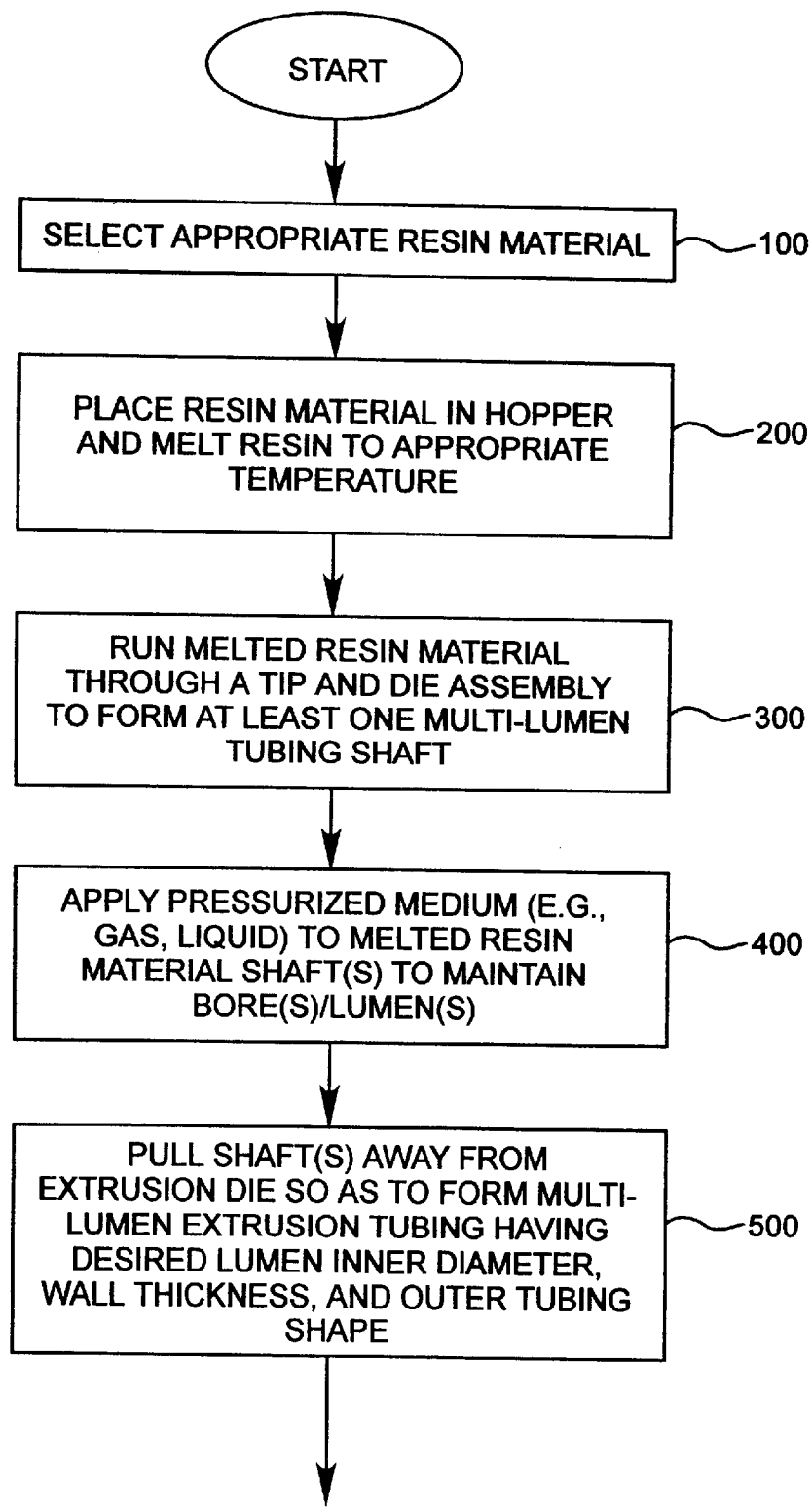
FIG. 26 is a flow chart illustrating a method of manufacture a multi-lumen balloon assembly of the present invention.
Figure 26:
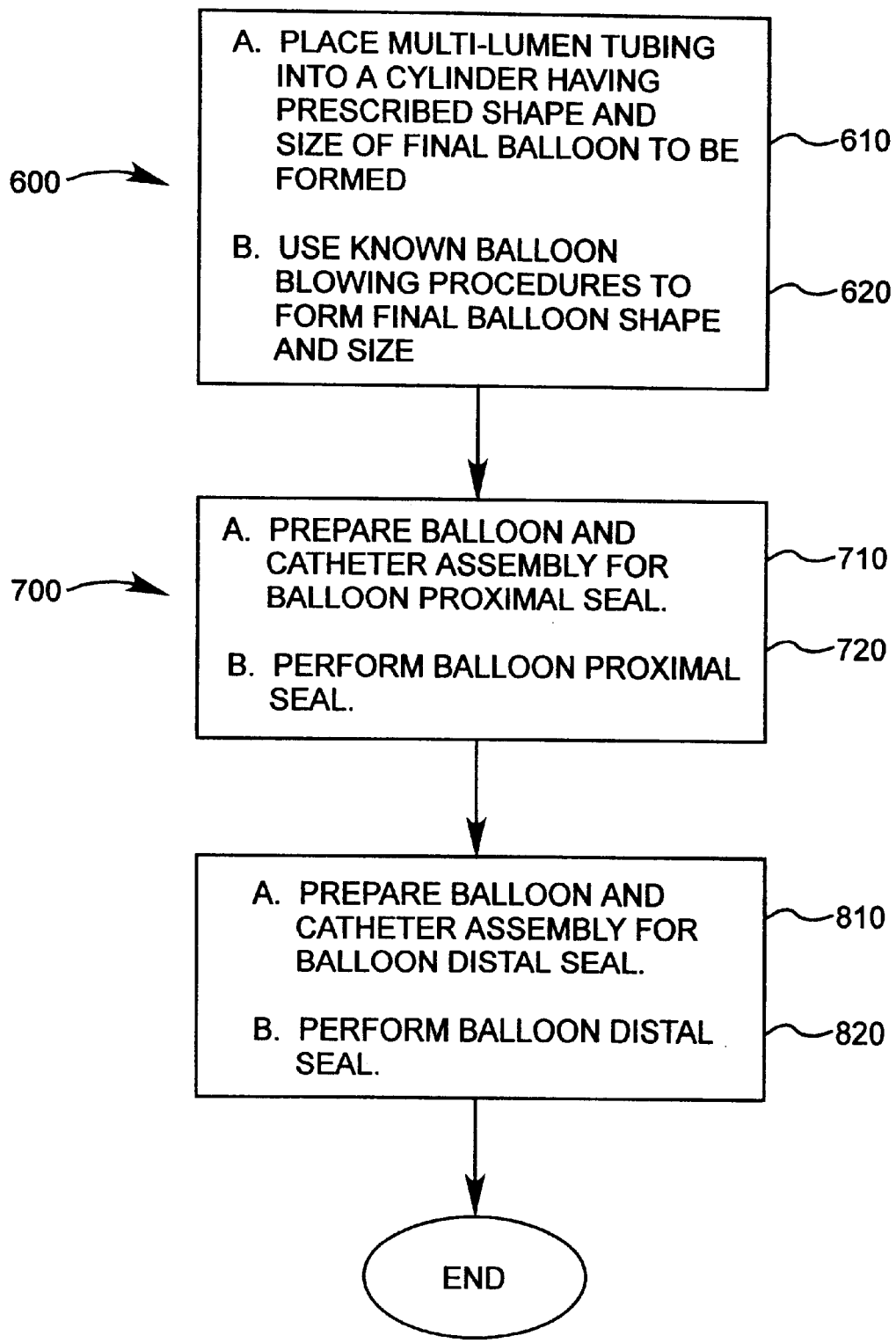

FIG. 26 is a flow chart illustrating the steps of fabricating a multi-lumen extruded tubing of one embodiment of the present invention, such as the multi-lumen extruded tubing for the radiation centering catheter shown in FIGS. 1, 6, 10, and 13.

Referring to FIG. 26, the first step in the extruded tubing manufacture process is to select an appropriate material from which the extruded tubing (and thus the balloon) will be manufactured (step 100). Recall that the multi-lumen extruded tubing is made of balloon materials known in the art of balloon angioplasty, such as Pebax™, nylon, polyethylene, polyurethane or polyester. Generally, any resin-type material may be used to manufacture the multi-lumen extruded tubing. Materials for use in fabricating the multi-lumen extruded tubing of the present invention are selected by considering the properties and characteristics (e.g., softness, durability) required by angioplasty balloons, as well as considering properties necessary for successful balloon fabrication (e.g., balloon material compatible with other catheter materials and bonding process, material extruding well, etc.).

At step 200 in the multi-lumen extruded tubing fabrication process, the resin material is placed into a hopper (or a similar. purpose receptacle) and is then gradually brought to a molten state.

The next three steps (Steps 300, 400, and 500) are performed concurrently during the multi-lumen extruded tubing manufacture process. In Step 300, the molten resin material is run through a tip and die assembly such that at least one multi-lumen shaft is formed. As part of Step 400, a pressurized medium (such as air or other gas) is applied into each of the lumens of the multi-lumen shaft (or the plurality of single lumen shafts) formed as part of Step 300 to maintain and/or control the inner diameter of the lumens (or bores) 63 formed lengthwise along the centerline of the shaft (or along a centerline of each of the plurality of shafts). If a pressurized gas is used, the pressurized gas applied to the plurality of resin material shafts may done at a pressure in the range of approximately 0–30 inches of water. In one embodiment, the pressurized gas applied to the plurality of resin material shafts is at a pressure of 2 inches of water.

Step 500 includes pulling the shaft (or depending on the extrusion die configuration, a plurality of shafts) away from the extrusion die (using a puller or similar device) so as to form the multi-lumen extruded tubing having the desired lumen inner diameter, lumen wall thickness, shared wall thickness, outer tubing shape, etc. Pulling the plurality of shafts away from the extrusion die (Step 500) may be done while the resin material is at a melt temperature in the range of about 370° F. to 440° F. In one embodiment, pulling the plurality of shafts away from the extrusion die is done while the resin material is at a melt temperature in the range of about 380° F. to 410° F. Pulling the plurality of resin material shafts away from the extrusion die may be done at a pulling rate of about 25–100 feet per minute. In one embodiment, pulling the plurality of resin material shafts away from the extrusion die is done at a pulling rate of about 45–65 feet per minute.

For extrusion die configurations that permit a plurality of shafts to be formed instead of a single shaft (as discussed below), Step 500 includes pulling the plurality of shafts away from the extrusion die so as to cause the plurality of shafts to fuse together lengthwise into the multi-lumen extrusion tubing having a central lumen and at least one outer lumen disposed adjacent to the central lumen.

Referring to FIGS. 22b–25b, several embodiments of a tip and die assembly of the present invention are shown. Each tip and die assembly includes an extrusion die (shown as 70, 170, 270, 370 in FIGS. 22b–25b) and a plurality of extrusion tip hypo-tubes (identified as: 71a, 171a, 271a, 371a in the figures) through which a pressurized medium (such as air, an inert gas, liquid, etc.) is introduced into the shaft's lumen to maintain and/or control the inner diameter of the lumen. The extrusion die may have a single common exit hole (item 76 in FIG. 22b and item 376 in FIG. 25b) or a plurality of exit holes (items 171, 172 in FIG. 23b and items 71, 72 in FIG. 24b). The hypo-tubes may take the form of mandrels (items 271a, 171a, 71a, and 371a in FIGS. 22b–25b) having a bore extending lengthwise through the center of the mandrels.

Continuing with reference to FIG. 22b, the extrusion die 270 is used in the manufacture of the multi-lumen extruded tubing 60 shown in FIG. 22a. The extrusion die 270 includes a single common exit hole 76 having a profile such that a multi-lumen extruded tubing 60 with a fillet radius region 66 disposed between the central lumen 62 and the plurality of outer lumens 63 is formed. The extrusion die 270 may be manufactured out of a metal, a hard plastic, or any other type of material used in medical extrusion tubing processes. Using a die with a single common exit hole simplifies the overall tubing extrusion process, thus permitting a multi-lumen single shaft to be more easily manufactured.

Referring to FIG. 23b, in a second embodiment of this invention, the extrusion die 170 is used in the manufacture of the multi-lumen extruded tubing 60 shown in FIG. 23a. The extrusion die 170 has at least one outer exit hole 171 disposed around a central exit hole 172. The outer exit hole 171 may be positioned at various distances 175 from the central exit hole 172. It may be desirable to place the outer exit hole 171 as close as possible to the central exit hole 172 in order to minimize the amount of resin material of the shared wall thickness 67b (shown in FIG. 23a). Having less resin material as part of the shared wall permits the multi-lumen tubing to blow better during the balloon forming process and ultimately leads to a less stiff balloon. The extrusion die 170 may be manufactured out of a metal, a hard plastic, or any other type of material used in medical extrusion tubing processes.

Referring to FIG. 24b, in a third embodiment of this invention, the extrusion die 70 is used in the manufacture of the multi-lumen extruded tubing 60 shown in FIG. 24a. The extrusion die 70 includes at least one outer exit hole 71 disposed around to a central exit hole 72. The outer exit hole 71 has a substantially flat shape across a part 73 of a periphery where the outer exit hole 71 is disposed adjacent to the central exit hole 72. The central exit hole 72 also has a substantially flat shape across a part 74 of a periphery where the central exit hole 72 is disposed adjacent to the outer exit hole 71.

The extrusion die 70 may be configured so that the outer exit hole 71 could be positioned at various die region thicknesses (or distances) 75 on the die region between the central exit hole 72 and outer exit hole 71. The die region thickness 75 may range from 0 in. to $^{10}/_{1000}$ in. In one embodiment, the die region thickness 75 between the central exit hole 72 and the outer exit hole 71 is about $^{5}/_{1000}$ in. It may be desirable to keep the die region thickness 75 to a thickness width such that when formed, the shared wall thickness 67b of the multi-lumen 60 is approximately equal to the outer lumen wall thickness 67c (see FIG. 24a). Having a shared wall thickness in the range of approximately 80% and 120% of the outer lumen wall thickness 67c minimizes the resin material of the shared wall and permits the multi-lumen tubing to blow better during the balloon forming process and ultimately leads to a less stiff balloon. The extrusion die 70 may be manufactured out of a metal, a hard plastic, or any other type of material used in medical extrusion tubing processes.

Referring to FIG. 25b, in a fourth embodiment of this invention, the extrusion die 370 is used in the manufacture of the multi-lumen extruded tubing 60 shown in FIG. 25a. The extrusion die 370 includes a single common exit hole 376 having a profile such that a multi-lumen extruded tubing 60 with at least one standoff region 64 disposed between the central lumen 62 and the outer lumens 63 is formed (see FIG. 25a). The extrusion die 370 may be manufactured out of a metal, a hard plastic, or any other type of material used in medical extrusion tubing processes. Using a die with a single common exit hole and having a profile with at least one standoff region minimize the amount of resin material between the central lumen 62 and plurality of outer lumens 63 (shown in FIG. 25a). Having less resin material permits the multi-lumen tubing 60 to blow better during the balloon forming process and ultimately leads to a less stiff balloon. Furthermore, using a die with a single common exit hole simplifies the overall tubing extrusion process, thus permitting a multi-lumen single shaft to be more easily manufactured.

The next step in the fabrication process, Steps 610 and 620, is to form the final balloon shape with multiple lumens. This is achieved by placing the multi-lumen extruded tubing obtained after completion of Steps 300–500 into a steel cylinder that is configured to have the appropriate shape of the final balloon.

Once the multi-lumen balloon is formed and shaped to the desired dimensions and configurations, the next steps include preparing the balloon and catheter assembly for the balloon proximal seal (Step 710) and performing the balloon proximal seal (Step 720). Step 810 includes preparing the balloon and catheter assembly for the balloon distal seal, while Step 820 includes performing the balloon distal seal.

In one embodiment of the present invention, laser bonding techniques are used to perform the proximal and distal seals. However, any seal bonding techniques known in the art of manufacture of angioplasty balloon catheters may be employed to achieve the seals.

Multi-Lumen Tubing—Alternate Method of manufacture: Dip Coating

An alternate method of manufacture of the multi-lumen balloon is by using a "Dip Coating" process. A description of this process and how the multi-lobed, multi-lumen balloon is made is presented herein.

First, a "mandrel" is obtained. The mandrel includes component elements (such as pins) that are sized and arranged such that they define the lumens (i.e., interior void spaces) of the intended multi-lumen balloon.

Next, the physical balloon elements (i.e., balloon lumens, thickness of balloon walls, etc.) are defined by applying a thin film of a pre-selected polymer (analogous to applying paint) on and about the pin. In one embodiment, the application of the thin film polymer is achieved by immersing the mandrel into a bath of the desired polymer. The polymer may be any polymer with properties that would lend themselves to dip coating such as the ability to go into solution or suspension with subsequent recovery of adequate film properties. Materials already used in this manner are for example: poly-urethanes, siloxanes or silicones, and latexes.

The thickness of the film (balloon wall) may be controlled by such factors as the viscosity of the bath solution and/or the number of times the mandrel is dipped into the solution. The "carrier" or "solvent" is then driven off (evaporated) by normal means such as time in ambient air or forced convection with or without added heat.

The balloon, if appropriate to the polymer selected, may be further processed to impart enhanced or additional properties such as irradiation to increase cross-linking. This can be achieved either before or after removing from the mandrel as appropriate to the material and/or properties and/or process.

In the next step, the film that is the balloon is then "stripped off" the mandrel through any appropriate means such as: using compressed air ported through the pins that make up the mandrel, swelling the balloon material with some other solvent which frees the balloon material from the mandrel and this solvent is then driven off returning the balloon to the original dimensions, mechanically stripping off the balloon, etc.

Finally, the balloon is trimmed and prepped as necessary for integration with the remaining catheter components.

A multi-lumen balloon for use in a fluted balloon centering catheter and method for providing the same has been described. Although specific embodiments, including specific parameters, methods, and materials have been described, various modifications to the disclosed embodiments will be apparent to one of ordinary skill in the art upon reading this disclosure. Therefore, it is to be understood that such embodiments are merely illustrative of and not restrictive on the broad invention and that this invention is not limited to the specific embodiments shown and described.

What is claimed is:

1. A method for making multi-lumen tubing, the method comprising:

pushing a molten resin material through a tip and die assembly such that a plurality of resin material shafts are formed, the tip and die assembly including an extrusion die and a plurality of mandrels, wherein the extrusion die has at least one outer exit hole disposed adjacent to a central exit hole;

applying a pressurized medium to the plurality of resin material shafts so as to maintain a lumen running lengthwise along the plurality of resin material shafts; and pulling the plurality of resin material shafts away from the extrusion die so as to cause the plurality of resin material shafts to fuse together lengthwise into the multi-lumen extrusion tubing having a central lumen and at least one outer lumen disposed adjacent to the central lumen.

2. The method of claim 1, wherein the at least one outer exit hole has a substantially flat shape across a part of a periphery where the at least one outer exit hole is disposed adjacent to the central exit hole.

3. The method of claim 1, wherein the central exit hole has a substantially flat shape across a part of a periphery where the central exit hole is disposed adjacent to the at least outer exit hole.

4. The method of claim 1 wherein said pulling the plurality of resin material shafts away from the extrusion die is done while the resin material is at a melt temperature in the range of about 370° F. to 440° F.

5. The method of claim 1 wherein said pulling the plurality of resin material shafts away from the extrusion die is done while the resin material is at a melt temperature in the range of about 380° F. to 410° F.

6. The method of claim 1 wherein the resin material is nylon.

7. The method of claim 1 wherein the resin material is polyethylene.

8. The method of claim 1 wherein the resin material is polyester.

9. The method of claim 1 wherein the pressurized medium comprises a pressurized gas.

10. The method of claim 9 wherein the pressurized gas applied to the plurality of resin material shafts is applied at a pressure of in a range of approximately 0–30 inches of water.

11. The method of claim 9 wherein the pressurized gas applied to the plurality of resin material shafts is applied at a pressure of 2 inches of water.

12. The method of claim 1 wherein the pressurized medium comprises air.

13. The method of claim 1 wherein said pushing a molten resin material through an extrusion die and said applying a pressurized fluid to the plurality of resin material shafts so as to maintain a lumen are performed concurrently.

14. The method of claim 1 wherein said pulling the plurality of resin material shafts away from the extrusion die is done at a pulling rate of about 25–100 feet per minute.

15. The method of claim 1 wherein said pulling the plurality of resin material shafts away from the extrusion die is done at a pulling rate of about 45–65 feet per minute.

16. The method of claim 1 wherein the at least one outer lumen has an outer lumen wall thickness in a range of approximately 0.0035–0.006 in.

17. The method of claim 1 wherein the multi-lumen tubing has an overall diameter in a range of approximately $34/1000$ in. to $48/1000$ in.

* * * * *